United States Patent [19]

Krüger et al.

[11] Patent Number: 5,679,676
[45] Date of Patent: Oct. 21, 1997

[54] SUBSTITUTED AZADIOXACYCLOALKENES AND THEIR USE AS FUNGICIDES

[75] Inventors: Bernd-Wieland Krüger, Bergisch Gladbach; Lutz Assmann, Eutin; Herbert Gayer, Monheim; Peter Gerdes, Aachen; Ulrich Heinemann, Leichlingen; Dietmar Kuhnt, Burscheid; Ulrich Philipp, Köln; Thomas Seitz, Langenfeld; Jörg Stetter, Wuppertal; Ralf Tiemann, Leverkusen; Heinz-Wilhelm Dehne, Bonn; Stefan Dutzmann, Hilden; Gerd Hänssler, Leverkusen, all of Germany

[73] Assignee: Bayer Aktiengesellschaft, Leverkusen, Germany

[21] Appl. No.: 596,175

[22] PCT Filed: Jul. 29, 1994

[86] PCT No.: PCT/EP94/02533

§ 371 Date: Feb. 5, 1996

§ 102(e) Date: Feb. 5, 1996

[87] PCT Pub. No.: WO95/04728

PCT Pub. Date: Feb. 16, 1995

[30] Foreign Application Priority Data

Aug. 11, 1993 [DE] Germany .................. 43 26 908.7
Mar. 10, 1994 [DE] Germany .................. 44 08 005.0

[51] Int. Cl.$^6$ .................. A61K 31/535; C07D 273/00
[52] U.S. Cl. .................. 514/229.2; 544/65; 540/544; 548/124
[58] Field of Search .................. 544/65; 514/229.2

[56] References Cited

FOREIGN PATENT DOCUMENTS

| 056 161 | 7/1982 | European Pat. Off. . |
|---------|--------|----------------------|
| 242 081 | 10/1987 | European Pat. Off. . |
| 528 681 | 2/1993 | European Pat. Off. . |
| A-01 221 371 | 9/1989 | Japan . |
| A-02 001 484 | 1/1990 | Japan . |

*Primary Examiner*—Mukund J. Shah
*Assistant Examiner*—Brenda Coleman
*Attorney, Agent, or Firm*—Sprung Horn Kramer & Woods

[57] ABSTRACT

The application relates to new azadioxacycloalkenes of the formula (I)

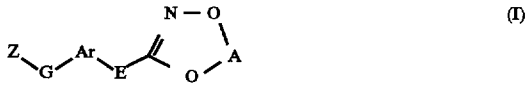

in which

Z, G, Ar, E and A have the meaning given in the description, to a process for their preparation, and to their use as fungicides.

7 Claims, No Drawings

SUBSTITUTED AZADIOXACYCLOALKENES AND THEIR USE AS FUNGICIDES

This application is a 371 or PCT/EP94/02533 filed Jul. 29, 1994.

The invention relates to novel substituted azadioxacycloalkenes, to a process for their preparation, and to their use as fungicides.

It has been disclosed that certain substituted 5,6-dihydro-1,4,2-dioxazines have fungicidal properties (cf. JP-A 01221371—cited in Chem. Abstracts 112: 98566t; JP 02001484—cited in Chem. Abstracts 113: 6381y).

However, these compounds have not gained particular importance.

The new substituted azadioxacycloalkenes of the general formula (I)

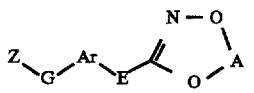

have now been found, in which

A represents optionally substituted alkanediyl (alkylene),

Ar represents in each case optionally substituted arylene or heteroarylene,

E represents a 1-alkene-1,1-diyl group with a radical $R^1$ in the 2-position, or a 2-aza-1-alkene-1,1-diyl group with a radical $R^2$ in the 2-position, or a 3-oxa- or 3-thia-1-propene-2,3-diyl group with a radical $R^1$ in the 1-position, or represents a 3-aza-1-propene-2,3-diyl group with a radical R in the 3-position and a radical $R^1$ in the 1-position, or represents a 1-aza-1-propene-2,3-diyl group with a radical $R^2$ in the 1-position, or represents a 3-oxa- or 3-thia-1-aza-propene-2,3-diyl group with a radical $R^2$ in the 1-position, or represents a 1,3-diaza-1-propene-2,3-diyl group with a radical R in the 3-position and a radical $R^2$ in the 1-position, or represents an optionally substituted imino group ("azamethylene", N—$R^3$), where R represents alkyl, $R^1$ represents hydrogen, halogen, cyano or in each case optionally substituted alkyl, alkoxy, alkylthio, alkylamino or dialkylamino, $R^2$ represents hydrogen, amino, cyano or in each case optionally substituted alkyl, alkoxy, alkylamino or dialkylamino, and $R^3$ represents hydrogen, cyano or in each case optionally substituted alkyl, alkenyl, alkinyl, cycloalkyl or cycloalkylalkyl, G represents a single bond, oxygen, or represents alkanediyl, alkenediyl, oxaalkenediyl, alkinediyl, each of which is optionally substituted by halogen, hydroxyl, alkyl, halogenoalkyl or cycloalkyl, or represents one of the groups below —Q—CQ—, —CQ—Q—, —CH$_2$—Q—, —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^4$)=N—O—, —C(R$^4$)=N—O—CH$_2$—, —N(R$^5$)—, —CQ—N(R$^5$)—, —N(R$^5$)—CQ—, —Q—CQ—N(R$^5$)—, —N=C(R$^4$)—Q—CH$_2$—, —CH$_2$—O—N=C(R$^4$)—, —N(R$^5$)—CQ—Q—, —CQ—N(R$^5$)—CQ—Q—, —N(R$^5$) —CQ—Q—CH$_2$—, —CQ—CH$_2$— or —N=N—C(R$^4$)=N—O—, where n represents the numbers 0, 1 or 2, Q represents oxygen or sulphur, $R^4$ represents hydrogen, cyano, or represents alkyl, alkoxy, alkylthio, alkylamino, dialkylamino or cycloalkyl, each of which is optionally substituted, and $R^5$ represents hydrogen, hydroxyl, cyano, or represents alkyl, alkoxy or cycloalkyl, each of which is optionally substituted, and Z represents in each case optionally substituted alkyl, alkenyl, alkinyl, cycloalkyl, aryl or heterocyclyl.

Furthermore, it has been found that the new substituted azadioxacycloalkenes of the general formula (I) are obtained when (a) carboxylic acid derivatives of the general formula (II)

in which

Ar, E, G and Z have the abovementioned meaning and R represents alkyl are reacted, in a first step, with hydroxylamine or with a hydrohalide thereof, if appropriate in the presence of an acid acceptor and if appropriate in the presence of a diluent, and the product of the first step is reacted in situ, i.e. without intermediate isolation, in a second step with disubstituted alkanes of the general formula (III),

in which

A has the abovementioned meaning and

X represents halogen; alkylsulphonyloxy or arylsulphonyloxy, if appropriate in the presence of an acid acceptor and, if appropriate, in the presence of a diluent, or when, (b) in the event that, in formula (I), G represents oxygen or the group —CH$_2$—O— and A, Ar, E and Z have the abovementioned meaning, hydroxyaryl compounds of the general formula (IV)

in which

A, Ar and E have the abovementioned meaning, are reacted with compounds of the general formula (V)

in which

X and Z have the abovementioned meaning and m represents the numbers 0 or 1, if appropriate in the presence of an acid acceptor and, if appropriate, in the presence of a diluent, and, if appropriate, substitution reactions are subsequently carried out on the group Z by customary methods, or when, (c) in the event that, in formula (I), G represents the group —Q—CH$_2$— and A, Ar, E and Z have the abovementioned meaning, halogenomethyl compounds of the general formula (VI)

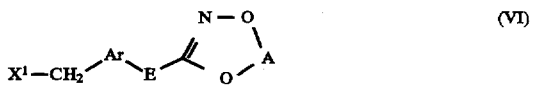

in which

A, Ar and E have the abovementioned meaning and $X^1$ represents halogen, are reacted with compounds of the general formula (VII)

3 in which

Q and Z have the abovementioned meaning, if appropriate in the presence of an acid acceptor and, if appropriate, in the presence of a diluent, or when (d) hydroxyalkoxyamides of the general formula (VIII)

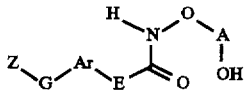

(VIII)

in which

A, Ar, E, G and Z have the abovementioned meaning, are subjected to a cyclization reaction with a dehydrating agent, if appropriate in the presence of a diluent.

Finally, it has been found that the new substituted aza-dioxacycloalkenes of the general formula (I) have a very powerful fungicidal activity.

Where appropriate, the compounds according to the invention can exist in the form of mixtures of various possible isomeric forms, in particular in the form of E- and Z-isomers. Claimed are the E- and Z-isomers and also any mixtures of these isomers.

The invention preferably relates to compounds of the formula (I) in which

A represents alkanediyl having 1 to 3 carbon atoms, which is optionally substituted by halogen or by alkyl or halogenoalkyl, each of which has 1 to 4 carbon atoms, Ar represents in each case optionally substituted phenylene or naphthylene, or represents heteroarylene having 5 or 6 ring members of which at least one represents oxygen, sulphur or nitrogen and, if appropriate, one or two further ring members represent nitrogen, the possible substituents preferably being selected from the list below:

halogen, cyano, nitro, amino, hydroxyl, formyl, carboxyl, carbamoyl, thiocarbamoyl, in each case straight-chain or branched alkyl, alkoxy, alkylthio, alkylsulphinyl or alkylsulphonyl, each of which has 1 to 6 carbon atoms, in each case straight-chain or branched alkenyl, alkenyloxy or alkinyloxy, each of which has 2 to 6 carbon atoms, in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl, each of which has 1 to 6 carbon atoms in the individual alkyl moieties, or represents in each case divalent alkylene or dioxyalkylene, each of which has 1 to 6 carbon atoms and each of which is optionally monosubstituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms, E represents one of the groups below

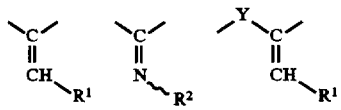

-continued

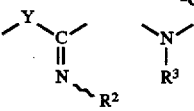

in which

Y represents oxygen, sulphur, methylene ($CH_2$) or alkylimino (N—R),

R represents alkyl having 1 to 6 carbon atoms, $R^1$ represents hydrogen, halogen, cyano, or represents alkyl, alkoxy, alkylthio, alkylamino or dialkylamino, each of which has 1 to 6 carbon atoms in the alkyl radicals and each of which is optionally substituted by halogen, cyano or $C_1$–$C_4$-alkoxy, $R^2$ represents hydrogen, amino, cyano, or represents alkyl, alkoxy, alkylamino or dialkylamino, each of which has 1 to 6 carbon atoms in the alkyl radicals and each of which is optionally substituted by halogen, cyano or $C_1$–$C_4$-alkoxy, and $R^3$ represents hydrogen, cyano, or represents alkyl, alkenyl or alkinyl, each of which has up to 6 carbon atoms and each of which is optionally substituted by halogen, cyano or $C_1$–$C_4$-alkoxy, or represents cycloalkyl or cycloalkylalkyl having 3 to 6 carbon atoms in the cycloalkyl moieties and, if appropriate, 1 to 4 carbon atoms in the alkyl moiety, each of these cycloalkyl or cycloalkylalkyl radicals optionally being substituted by halogen, cyano, carboxyl, $C_1$–$C_4$-alkyl or $C_1$–$C_4$-alkoxy-carbonyl, G represents a single bond, oxygen, or represents alkanediyl, alkenediyl, oxaalkenediyl, alkinediyl, each of which has up to 4 carbon atoms and each of which is optionally substituted by halogen, hydroxyl, $C_1$–$C_4$-alkyl, $C_1$–$C_4$-halogenoalkyl or $C_3$–$C_6$-cycloalkyl, or represents one of the groups below —Q—CQ—, —CQ—Q—, —$CH_2$—Q—, —Q—$CH_2$—, —CQ—Q—$CH_2$—, —$CH_2$—Q—CQ—, —Q—CQ—Q—$CH_2$—, —Q—CQ—Q—$CH_2$—, —N=N—, —S(O)$_n$—, —$CH_2$—S(O)$_n$—, —CQ—, —S(O)$_n$—$CH_2$—, —C($R^4$)=N—O—, —C($R^4$)=N—O—$CH_2$—, —N($R^5$)—, —CQ—N($R^5$)—, —N($R^5$)—CQ—, —Q—CQ—N($R^5$)—, —N=C($R^4$)—Q—$CH_2$—, —$CH_2$—O—N=C($R^4$)—, —N($R^5$)—CQ—Q—, —CQ—N($R^5$)—CQ—Q—, —N($R^5$)—CQ—Q—$CH_2$—, —CQ—$CH_2$— or —N=N—C($R^4$)=N—O—, where n represents the numbers 0, 1 or 2, Q represents oxygen or sulphur, $R^4$ represents hydrogen, cyano, or represents alkyl, alkoxy, alkylthio, alkylamino or dialkylamino, each of which has 1 to 6 carbon atoms in the alkyl groups and each of which is optionally substituted by halogen, cyano or $C_1$–$C_4$-alkoxy, or represents cycloalkyl having 3 to 6 carbon atoms which is optionally substituted by halogen, cyano, carboxyl, $C_1$–$C_4$-alkyl or $C_1$–$C_4$-alkoxy-carbonyl, and $R^5$ represents hydrogen, hydroxyl, cyano, or represents alkyl having 1 to 6 carbon atoms which is optionally substituted by halogen, cyano or $C_1$–$C_4$-alkoxy, or represents cycloalkyl having 3 to 6 carbon atoms which is optionally substituted by halogen, cyano, carboxyl, $C_1$–$C_4$-alkyl or $C_1$–$C_4$-alkoxy-carbonyl, and Z represents alkyl having 1 to 8 carbon atoms which is optionally substituted by halogen, cyano, hydroxyl, amino, $C_1$–$C_4$-alkoxy, $C_1$–$C_4$-alkylthio, $C_1$–$C_4$-alkyl-sulphinyl or $C_1$–$C_4$-alkylsulphonyl (each of which is optionally substituted by halogen), or represents alkenyl or alkinyl, each of which has up to 8 carbon atoms and each of which is optionally substituted by halogen, or represents cycloalkyl having 3 to 6 carbon atoms which is optionally substituted by halogen, cyano, carboxyl, phenyl (which is optionally substituted by halogen, cyano, $C_1$-$C_4$-alkyl, $C_1$-$C_4$-halogenoalkyl, $C_1$-$C_4$-alkoxy or $C_1$-$C_4$-halogenoalkoxy), $C_1$-$C_4$-alkyl or $C_1$-$C_4$-alkoxy-carbonyl, or represents in each case optionally substituted phenyl, naphthyl or (optionally benzo-fused) heterocyclyl having 5 or 6 ring members of which at least one represents oxygen, sulphur or nitrogen and, if appropriate, one or two further ring members represent nitrogen, other possible substituents preferably being selected from the list below:

oxygen (as a replacement for two geminal hydrogen atoms), halogen, cyano, nitro, amino, hydroxyl, formyl, carboxyl, carbamoyl, thiocarbamoyl, in each case straight-chain or branched alkyl, alkoxy, alkylthio, alkylsulphinyl or alkylsulphonyl, each of which has 1 to 6 carbon atoms, in each case straight-chain or branched alkenyl or alkenyloxy, each of which has 2 to 6 carbon atoms, in each case straight-chain or branched halogenoalkyl, halogeno-alkoxy, halogenoalkylthio, halogenoalkylsulphinyl or halogenoalkylsulphonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl, each of which has 1 to 6 carbon atoms in the individual alkyl moieties, in each case divalent alkylene or dioxyalkylene, each of which has 1 to 6 carbon atoms and each of which is optionally mono-substituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms, or cycloalkyl having 3 to 6 carbon atoms, heterocyclyl or heterocyclyl-methyl, each of which has 3 to 7 ring members, of which in each case 1 to 3 are identical or different hetero atoms—in particular nitrogen, oxygen and/or sulphur-, and phenyl, phenoxy, benzyl, benzyloxy, phenylethyl or phenylethyloxy, each of which is optionally monosubstituted or polysubstituted in the phenyl moiety by identical or different substituents from the series consisting of halogen, cyano, nitro, carboxyl, carbamoyl and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy having 1 to 4 carbon atoms and/or straight-chain or branched halogenoalkoxy having 1 to 4 carbon atoms and 1 to 9 identical or different halogen atoms and/or alkylcarbonyl or alkoxycarbonyl, each of which has up to 5 carbon atoms.

The saturated or unsaturated hydrocarbon chains in the definitions, such as alkyl, alkanediyl, alkenyl or alkinyl, also together with hetero atoms, such as in alkoxy, alkylthio or alkylamino, are in each case straight-chain or branched.

Halogen generally represents fluorine, chlorine, bromine or iodine, preferably fluorine, chlorine or bromine, in particular fluorine or chlorine.

In particular, the invention relates to compounds of the formula (I) in which

A represents methylene or dimethylene (ethane-1,2-diyl) each of which is optionally substituted by fluorine, chlorine, methyl, ethyl or trifluoromethyl, Ar represents in each case optionally substituted ortho-, meta- or para-phenylene, or represents furandiyl, thiophenediyl, pyrrolediyl, pyrazolediyl, triazolediyl, oxazolediyl, isoxazolediyl, thiazolediyl, isothiazolediyl, oxadiazolediyl, thiadiazolediyl, pyridinediyl, pyrimidinediyl, pyridazinediyl, pyrazinediyl, 1,3,4-triazinediyl or 1,2,3-triazinediyl, the possible substituents being selected, in particular, from the list below:

fluorine, chlorine, cyano, methyl, ethyl, trifluoromethyl, methoxy, ethoxy, methylthio, methylsulphinyl or methylsulphonyl, E represents one of the groups below

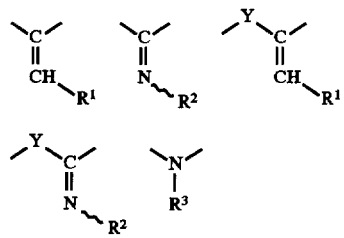

in which

Y represents oxygen, sulphur, methylene ($CH_2$) or alkylimino (N—R),

R represents methyl, ethyl, n- or i-propyl, or n-, i- or s-butyl, $R^1$ represents hydrogen, fluorine, chlorine, bromine, cyano, or represents methyl, ethyl, propyl, methoxy, ethoxy, methylthio, ethylthio, methylamino, ethylamino or dimethylamino, each of which is optionally substituted by fluorine, chlorine, cyano, methoxy or ethoxy, $R^2$ represents hydrogen, amino, cyano, or represents methyl, ethyl, methoxy, ethoxy, methylamino, ethylamino or dimethylamino, each of which is optionally substituted by fluorine, chlorine, cyano, methoxy or ethoxy, and $R^3$ represents hydrogen, cyano, or represents methyl, ethyl, n- or i-propyl or n-, i- or s-butyl, each of which is optionally substituted by fluorine, cyano, methoxy or ethoxy, represents allyl or propargyl, or represents cyclopropyl, cyclobutyl, cyclopentyl, cyclohexyl, cyclopropylmethyl, cyclobutylmethyl, cyclopentylmethyl or cyclohexylmethyl, each of which is optionally substituted by fluorine, chlorine, cyano, carboxyl, methyl, ethyl, n- or i-propyl, methoxy-carbonyl or ethoxy-carbonyl, G represents a single bond, oxygen, or represents methylene, dimethylene (ethane-1,2-diyl), ethene-1,2-diyl, ethine-1,2-diyl, each of which is optionally substituted by fluorine, chlorine, hydroxyl, methyl, ethyl, n- or i-propyl, trifluoromethyl, cyclopropyl, cyclobutyl, cyclopentyl or cyclohexyl, or represents one of the groups below —Q—CQ—, —CQ—Q—, —$CH_2$—Q—, —Q—$CH_2$—, —CQ—Q—$CH_2$—, —$CH_2$—Q—CQ—, —Q—CQ—$CH_2$—, —Q—CQ—Q—$CH_2$—, —N=N—, —S(O)$_n$—, —$CH_2$—S(O)$_n$—, —CQ—, —S(O)$_n$—$CH_2$—, —C($R^4$)=N—O—, —C($R^4$)=N—O—$CH_2$—, —N($R^4$)—, —CQ—N($R^5$)—, —N($R^5$)—CQ—, —Q—CQ—N($R^5$)—, —N=C($R^4$)—Q—$CH_2$—, —$CH_2$—O—N=C($R^4$)—, —N($R^5$)—CQ—Q—, —CQ—N($R^5$)—CQ—Q— or —N($R^5$)—CQ—Q—$CH_2$—, where n represents the numbers 0, 1 or 2, Q represents oxygen or sulphur, $R^4$ represents hydrogen, cyano, or represents methyl, ethyl, n- or i-propyl, n-, i- or s-butyl, methoxy, ethoxy, propoxy, butoxy, methylthio, ethylthio, propylthio, butylthio, methylamino, ethylamino, propylamino, dimethylamino or diethylamino, each of which is optionally substituted by fluorine, chlorine, cyano, methoxy or ethoxy, or represents cyclopropyl, cyclobutyl, cyclopentyl or cyclohexyl, each of which is optionally substituted by fluorine, chlorine, cyano, carboxyl, methyl, ethyl, n- or i-propyl, methoxycarbonyl or ethoxy-carbonyl, and R$^3$ represents hydrogen, hydroxyl, cyano, or represents methyl, ethyl, n- or i-propyl, n-, i-, s- or t-butyl, each of which is optionally substituted by fluorine, chlorine, cyano, methoxy or ethoxy, or represents cyclopropyl, cyclobutyl, cyclopentyl or cyclohexyl, each of which is optionally substituted by fluorine, chlorine, cyano, carboxyl, methyl, ethyl, n- or i-propyl, methoxy-carbonyl or ethoxy-carbonyl, and Z represents methyl, ethyl n- or i-propyl or n-, i-, s- or t-butyl, each of which is optionally substituted by fluorine, chlorine, bromine, cyano, hydroxyl, amino, methoxy, ethoxy, methylthio, ethylthio, methylsulphinyl, ethylsulphinyl, methylsulphonyl or ethylsulphonyl (each of which is optionally substituted by fluorine and/or chlorine), or represents allyl, crotonyl, 1-methyl-allyl, propargyl or 1-methyl-propargyl, each of which is optionally substituted by fluorine, chlorine or bromine, or represents cyclopropyl, cyclobutyl, cyclopentyl or cyclohexyl, each of which is optionally substituted by fluorine, chlorine, bromine, cyano, carboxyl, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, n- or i-propyl, methoxycarbonyl or ethoxy-carbonyl, or represents in each case optionally substituted phenyl, naphthyl, furyl, tetrahydrofuryl, benzofuryl, tetrahydropyranyl, thienyl, benzothienyl, pyrrolyl, dihydropyrrolyl, tetrahydropyrrolyl, benzopyrrolyl, benzodihydropyrrolyl, oxazolyl, benzoxazolyl, isoxazolyl, thiazolyl, benzothiazolyl, isothiazolyl, imidazolyl, benzimidazolyl, oxadiazolyl, thiadiazolyl, pyridinyl, pyrimidinyl, pyridazinyl, pyrazinyl, 1,2,3-triazinyl, 1,2,4-triazinyl or 1,3,5-triazinyl, the possible substituents preferably being selected from the list below:

oxygen (as a replacement for two geminal hydrogen atoms), fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluoromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl; or trimethylene (propane-1,3-diyl), methylenedioxy or ethylenedioxy, each of which is optionally monosubstituted or polysubstituted by identical or different substituents from the series consisting of fluorine, chlorine, methyl, ethyl or n- or i-propyl, or cyclopropyl, cyclobutyl, cyclopentyl or cyclohexyl, and phenyl, phenoxy, benzyl or benzyloxy, each of which is optionally monosubstituted or polysubstituted in the phenyl moiety by identical or different substituents from the series consisting of fluorine, chlorine, bromine, cyano, nitro, carboxyl, carbamoyl, methyl, ethyl, n- or i-propyl, n-, i-, s - or t-butyl, trifluoromethyl, methoxy, ethoxy, n- or i-propoxy, difluoromethoxy, trifluoromethoxy, acetyl, methoxycarbonyl or ethoxycarbonyl.

A particularly preferred group of compounds according to the invention are those compounds of the formula (I) in which A represents dimethylene (ethane-1,2-diyl), Ar represents ortho-phenylene, pyridine-2,3-diyl or thiophene-2,3-diyl, E represents one of the groups below

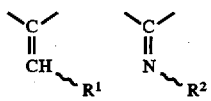

in which

R$^1$ and R$^2$ in each case represent methoxy,

G represents oxygen, methylene or one of the groups below

—CH$_2$—O—, —O—CH$_2$—, —S(O)n—, —CH$_2$—S(O)$_n$—, —S(O)$_n$—CH$_2$—, —C(R$^4$)=N—O—, —O—N=C(R$^4$)—, —C(R$^4$)=N—O—CH$_2$—, —N(R$^5$)— or —CH$_2$—O—N=C(R$^4$)—, where n represents the numbers 0, 1 or 2, R$^4$ represents hydrogen, methyl or ethyl and R$^5$ represents hydrogen, methyl or ethyl, and Z represents in each case optionally substituted phenyl, pyridinyl, pyrimidinyl, pyridazinyl, pyrazinyl, 1,2,3-triazinyl, 1,2,4-triazinyl or 1,3,5-triazinyl, the possible substituents preferably being selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i- propylthio, methylsulphinyl, ethylsulphinyl, methylsulphonyl or ethylsulphonyl, trifluoromethyl, difluoromethoxy, trifluoromethoxy, difluoromethylthio, trifluoromethylthio, trifluoromethylsulphinyl or trifluoromethylsulphonyl, methoxycarbonyl, ethoxycarbonyl, methoximinomethyl, ethoximinomethyl, methoximinoethyl or ethoximinoethyl, or methylenedioxy or ethylenedioxy, each of which is optionally monosubstituted or polysubstituted by identical or different substituents from the series consisting of fluorine, chlorine, methyl or ethyl, and phenyl, phenoxy, benzyl or benzyloxy, each of which is optionally monosubstituted or polysubstituted in the phenyl moiety by identical or different substituents from the series consisting of fluorine, chlorine, bromine, cyano, methyl, ethyl, n- or i-propyl, n-, i -, s - or t-butyl, trifluoromethyl, methoxy,- ethoxy, n- or i-propoxy, difluoromethoxy or trifluoromethoxy.

The abovementioned general definitions of radicals, or definitions of radicals where preferred ranges have been indicated, apply to the end product of the formula (I) and, analogously, to the starting substances or intermediates required in each case for their preparation.

These definitions of radicals can be combined with each other as desired, that is to say combinations between the ranges of preferred compounds which have been indicated are also possible.

If, for example, methyl α-methoximino-α-(2-phenoxyphenyl)-acetate, hydroxylamine hydrochloride and 1,2-dibromo-ethane are used as starting substances, the course of the reaction in preparation process (a) according to the invention can be outlined by the following equation:

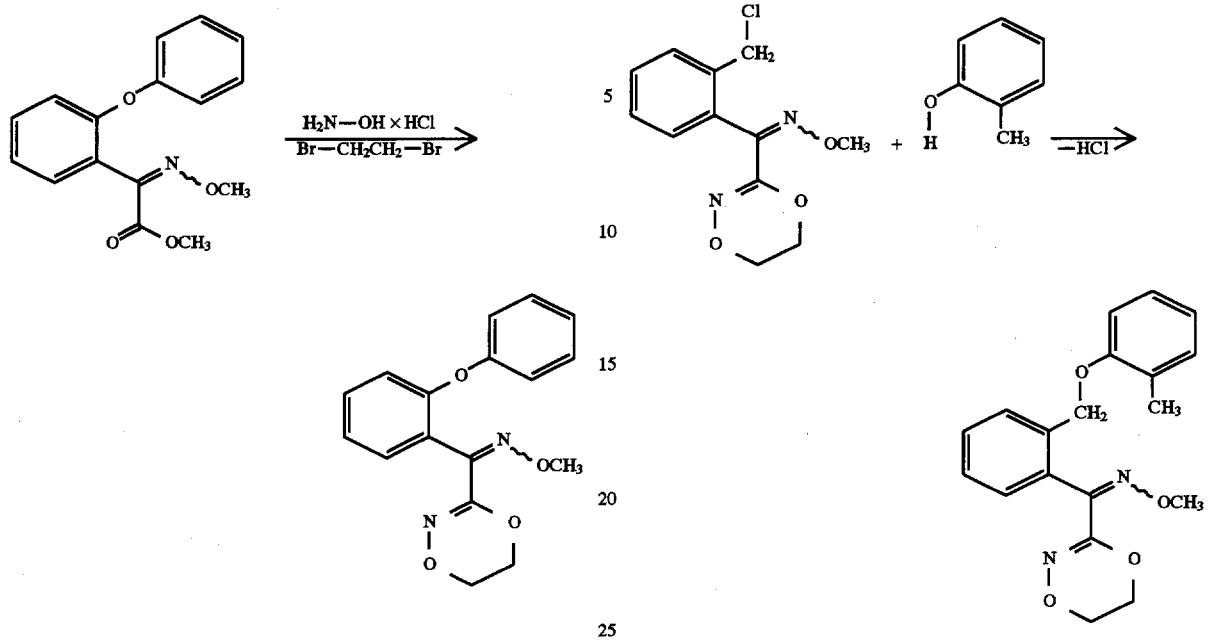

If, for example, 3-[α-methoximino-α-(2-hydroxy-phenyl)methyl]-5,6-dihydro-1,4,2-dioxazine and benzyl chloride are used as starting substances, the course of the reaction in preparation process (b) according to the invention can be outlined by the following equation:

If, for example, N-(2-hydroxy-ethoxy)-α-methoximino-α-(2-phenoxy-phenyl)-acetamide is used as starting compound, the course of the reaction in the preparation process according to the invention can be outlined by the following equation:

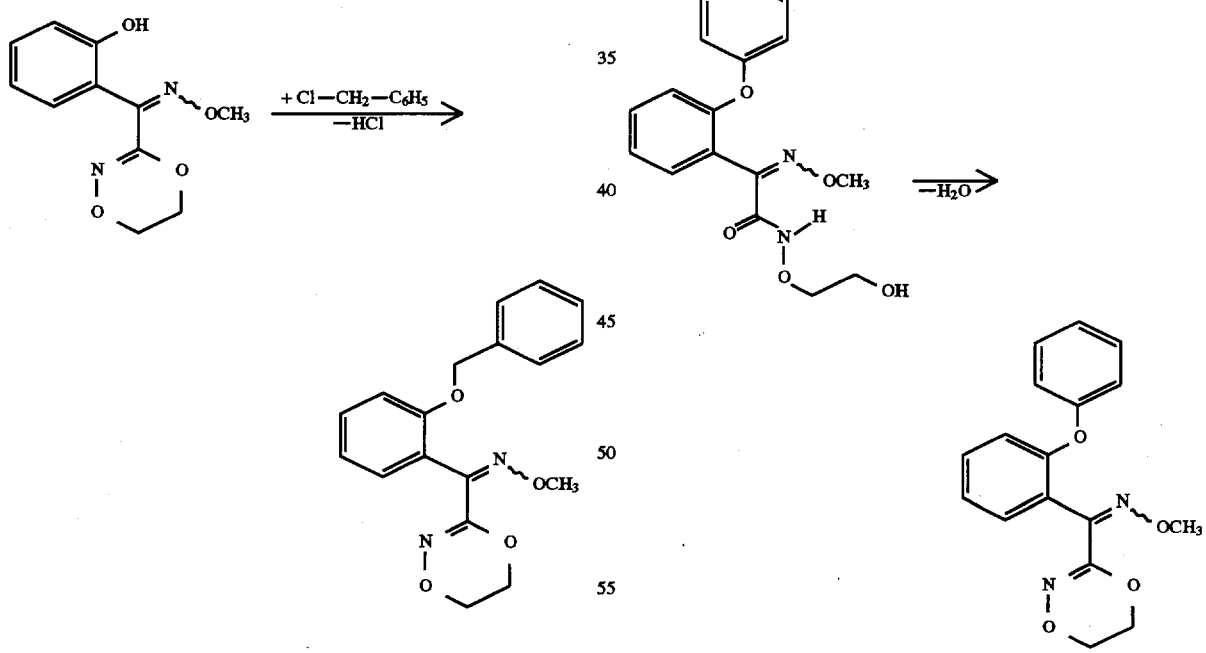

If, for example, 3-[α-methoximino-α-(2-chloromethylphenyl)-methyl]-5,6-dihydro-1,4,2-dioxazine and 2-methylphenol are used as starting substances, the course of the reaction in preparation process (c) according to the invention can be outlined by the following equation:

Formula (II) provides a general definition of the carboxylic acid derivatives required as starting substances for carrying out process (a) according to the invention. In this formula (II), Ar, E, G and Z preferably, or in particular, have the meanings which have already been mentioned in connection with the description of the compounds of the formula (I) according to the invention as being preferred, or particularly preferred, for Ar, E, G and Z; R preferably represents alkyl having 1 to 4 carbon atoms, in particular methyl or ethyl.

The starting substances of the formula (II) are known and/or can be prepared by processes known per se (cf. EP-A 178826, EP-A 242081, EP-A 382375, EP-A 493711).

Formula (III) provides a general definition of the disubstituted alkanes furthermore to be used as starting substances in process (a) according to the invention. In formula (III), A preferably, or in particular, has that meaning which has already been given in connection with the description of the compounds of the formula (I) according to the invention as being preferred, or particularly preferred, for A; X preferably represents chlorine, bromine, methylsulphonyloxy, phenylsulphonyloxy or tolylsulphonyloxy.

The starting substances of the formula (III) are known chemicals for organic synthesis.

Formula (IV) provides the general definition of the hydroxyaryl compounds to be used as starting substances in process (b) according to the invention for the preparation of the compounds of the general formula (I). In formula (IV), A, Ar and E preferably, or in particular, have those meanings which have already been given above in connection with the description of the compounds of the formula (I) as being preferred, or particularly preferred, for A, Ar and E.

The starting substances of the formula (IV) were hitherto not known from the literature; as new substances, they are part of the present application.

The new hydroxyaryl compounds of the formula (IV) are obtained when tetrahydropyranyloxy compounds of the general formula (IX)

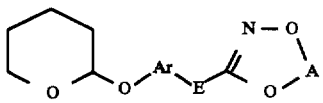

(IX)

in which

A, Ar and E have the abovementioned meaning, are reacted with an acid, such as, for example, hydrochloric acid, sulphuric acid, methanesulphonic acid, benzenesulphonic acid, p-toluenesulphonic acid, or with an acidic ion exchanger, if appropriate in the presence of a diluent, such as, for example, water, methanol, ethanol or ethyl acetate, at temperatures between 0° C. and 100° C. (cf. the Preparation Examples).

The tetrahydropyranyloxy compounds of the formula (IX) were hitherto not known from the literature; as new substances, they are part of the present application.

The new tetrahydropyranyloxy compounds of the formula (IX) are obtained when esters of the general formula (X)

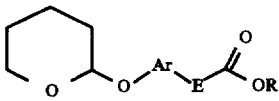

(X)

in which

Ar, E and R have the abovementioned meaning, are reacted with hydroxylamine—or, if appropriate, with the hydrochloride thereof—if appropriate in the presence of an acid acceptor, such as, for example, potassium hydroxide, and, if appropriate, in the presence of diluents, such as, for example, methanol and water, and the intermediate formed is reacted further in situ with dihalogenoalkanes of the general formula (III)—above—if appropriate in the presence of an acid acceptor, such as, for example, potassium carbonate, at temperatures between 0° C. and 100° C. (cf. the description of process (a) according to the invention and the Preparation Examples).

The esters of the formula (X) were hitherto not known from the literature; as new substances, they are part of the present application.

The new esters of the formula (X) are obtained when tetrahydropyranyloxy-phenylacetic esters of the general formula (XI)

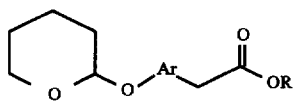

(XI)

in which

Ar and R have the abovementioned meaning are derivatized by customary methods (cf. the Preparation Examples).

The tetrahydropyranyloxy-phenylacetic esters of the formula (XI) were hitherto not known from the literature; as new substances, they are part of the present application.

The new tetrahydropyranyloxy-phenylacetic esters of the formula (XI) are obtained when hydroxyphenylacetic esters of the general formula (XII)

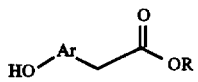

(XII)

in which

Ar and R have the abovementioned meaning are reacted with dihdyropyran, if appropriate in the presence of a catalyst, such as, for example, p-toluenesulphonic acid, and, if appropriate, in the presence of a diluent, such as, for example, tetrahydrofuran, at temperatures between 0° C. and 100° C. (cf. the Preparation Examples).

The starting substances of the formula (XII) are known chemicals for synthesis.

Formula (V) provides a general definition of the compounds furthermore to be used as starting substances in process (b) according to the invention for the preparation of the compounds of the general formula (I). In formula (V), Z preferably, or in particular, has that meaning which has already been mentioned above in connection with the description of the compounds of the formula (I) as being preferred, or particularly preferred, for Z; X preferably represents chlorine, bromine, methylsulphonyloxy, phenylsulphonyloxy or tolylsulphonyloxy.

The starting substances of the formula (V) are known chemicals for synthesis.

Formula (VI) provides a general definition of the halogenomethyl compounds to be used as starting substances in process (c) according to the invention for the preparation of the compounds of the general formula (I). In formula (VI), A, Ar and E preferably, or in particular, have those meanings which have already been mentioned above in connection with the description of the compounds of the formula (I) as being preferred, or particularly preferred, for A, Ar and E; $X^1$ preferably represents fluorine, chlorine, bromine or iodine, in particular chlorine or bromine.

The starting substances of the formula (VI) were hitherto not known from the literature; as new substances, they are part of the present application.

The new halogenomethyl compounds of the formula (VI) are obtained when methyl compounds of the general formula (XIII)

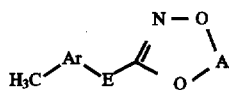 (XIII)

in which

A, Ar and E have the abovementioned meaning are reacted with a halogenating agent such as, for example, N-bromo- or N-chloro-succinimide, at temperatures between 0° C. and 150° C., if appropriate in the presence of a catalyst, such as, for example, azoisobutyronitrile and, if appropriate, in the presence of a diluent, such as, for example, tetrachloromethane (cf. the Preparation Examples).

The methyl compounds of the formula (XIII) required as precursors were hitherto not known from the literature; as new substances, they are part of the present application.

The new methyl compounds of the formula (XIII) are obtained when esters of the general formula (XIV)

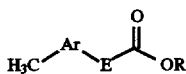 (XIV)

in which

A, E and R have the abovementioned meaning are reacted with hydroxylamine or hydroxylamine hydrochloride, if appropriate in the presence of an acid acceptor, such as, for example, potassiumhydroxide, and, if appropriate, in the presence of a diluent, such as, for example, methanol, and the product is then reacted with a disubstituted alkane of the general formula (III)—above—at temperatures between 0° C. and 150° C. analogously to process (a) according to the invention, if appropriate in the presence of an acid acceptor, such as, for example, potassium carbonate (cf. the Preparation Examples).

The precursors of the formula (XIV) are known and/or can be prepared by processes known per se (cf. EP-A 386561, EP-A 498188, Preparation Examples).

Formula (VII) provides a general definition of the compounds furthermore to be used as starting substances in process (c) according to the invention for the preparation of the compounds of the general formula (I). In formula (VII), Q and Z preferably, or in particular, have those meanings which have already been given above in connection with the description of the compounds of the formula (I) as being preferred, or particularly preferred, for Q and Z.

The starting substances of the formula (VII) are known chemicals for organic synthesis. Formula (VIII) provides a general definition of the hydroxyalkoxyamides to be used as starting substances in process (d) according to the invention for the preparation of the compounds of the general formula (I). In formula (VIII), A, Ar, E, G and Z preferably, or in particular, have those meanings which have already been given above in connection with the description of the compounds of the formula (I) as being preferred, or particularly preferred, for A, Ar, E, G and Z.

The starting substances of the formula (XIII) were hitherto not known from the literature; as new substances, they are part of the present application.

The new hydroxyalkoxyamides of the formula (VIII) are obtained when carboxylic acid derivatives of the general formula (XV)

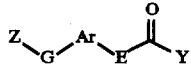 (XV)

in which

Ar, E, G and Z have the abovementioned meaning and Y represents halogen, hydroxyl or alkoxy are reacted with hydroxylsmines of the general formula (XVI)

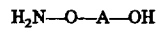 (XVI)

$H_2N-O-A-OH$ in which

A has the abovementioned meaning at temperatures between 0° C. and 150° C., if appropriate in the presence of an acid acceptor, such as, for example, triethylemine, pyridine or 4-dimethylemino-pyridine, and, if appropriate, in the presence of a diluent, such as, for example, methylene chloride, toluene or tetrahydrofuran (cf. the Preparation Examples).

The carboxylic acid derivatives of the formula (XV), which are required as precursors, are known and/or can be prepared by processes known per se (cf. EP-A 178826, EP-A 242081, EP-A 382375, EP-A 493711).

The hydroxylamines of the formula (XVI), which are furthermore required as precursors, are also known and/or can be prepared by processes known per se (cf. J. Chem. Soc. Perkin Trans. I 1987, 2829–2832).

Processes (a), (b) and (c) according to the invention are preferably carried out in the presence of a suitable acid acceptor. Suitable acid acceptors are all customary inorganic or organic bases. These include, for example, the hydrides, hydroxides, amides, alcoholares, acetates, carbonates or hydrogen carbonates of alkaline earth metals or alkali metals, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and also tertiary amines, such as trimethylamine, triethylamine, tributylamine, N,N-dimethylaniline, N,N-dimethyl-benzylamine, pyridine, N-methylpiperidine, N,N-dimethylaminopyridine, diazabicyclooctane (DABCO), diazabicyclononene (DBN) or diazabicycloundecene (DBU).

Suitable diluents for carrying out processes (a), (b) and (c) according to the invention are water and organic solvents. These include, in particular, aliphatic, allcyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, tetrachloromethane, ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketones, nitriles, such as acetonltrile, propionitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, their mixtures with water, or pure water.

Process (d) according to the invention is preferably carried out in the presence of a dehydrating agent. Suitable dehydrating agents are the customary dehydrating chemicals, in particular acid anhydrides, such as, for example, phosphorus(V) oxide (phosphorus pentoxide).

Suitable diluents for carrying out process (d) according to the invention are the customary inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, tetrachloromethane; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide.

When carrying out processes (a), (b), (c) and (d) according to the invention, the reaction temperatures can be varied within a substantial range. In general, the processes are carried out at temperatures between −20° C. and +200° C., preferably at temperatures between 0° C. and 150° C.

To carry out process (a) according to the invention, in general 1 to 5 mol, preferably 1.0 to 2.5 mol, of hydroxylamine or hydroxylamine hydrohalide and in general 1 to 10 mol, preferably 1.0 to 5.0 mol, of a disubstituted alkane of the formula (III) are employed per mole of carboxylic acid derivative of the formula (II).

To carry out process (b) according to the invention, in general 0.5 to 2.0 mol, preferably 0.9 to 1.2 mol, of a compound of the formula (V) are employed per mole of hydroxyaryl compound of the formula (IV).

To carry out process (c) according to the invention, in general 1 to 5 mol, preferably 1.5 to 3 mol, of a compound of the formula (VII) are employed per mole of halogen compound of the formula (IV).

To carry out process (d) according to the invention, in general 1 to 5 mol, preferably 1.5 to 4 mol, of a dehydrating agent are employed per mole of hydroxyalkoxyamide of the formula (VIII).

The reaction is carried out and the reaction products are worked up and isolated in each case by known methods (cf. the Preparation Examples).

The active compounds according to the invention have a powerful microbicidal activity and can be employed in practice for combating undesired microorganisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as *Pythium ultimum;*

Phytophthora species, such as *Phytophthora infestans;*

Pseudoperonospora species, such as *Pseudoperonospora humuli* or *Pseudoperonospora cubensis;*

Plasmopara species, such as *Plasmopara viticola;*

Peronospora species, such as *Peronospora pisi* or *Peronospora brassicae;*

Erysiphe species, such as *Erysiphe graminis;*

Sphaerotheca species, such as *Sphaerotheca fuliginea;*

Podosphaera species, such as *Podosphaera leucotricha;*

Venturia species, such as *Venturia inaequalis;*

Pyrenophora species, such as *Pyrenophora teres* or *Pyrenophora grauninea* (conidia form: Drechslera, syn: Helminthosporium);

Cochliobolus species, such as *Cochliobolus sativus* (conidia form: Drechslera, syn: Helminthosporium);

Uromyces species, such as *Uromyces appendiculatus;*

Puccinia species, such as *Puccinia recondita;*

Tilletia species, such as *Tilletia caries;*

Ustilago species, such as *Ustilago nuda* or *Ustilago avenae;*

Pellicularia species, such as *Pellicularia sasakii;*

Pyricularia species, such as *Pyricularia oryzae;*

Fusarium species, such as *Fusarium culmorum;*

Botrytis species, such as *Botrytis cinerea;*

Septoria species, such as *Septoria nodorum;*

Leptosphaeria species, such as *Leptosphaeria nodorum;*

Cercospora species, such as *Cercospora canescens;*

Alternaria species, such as *Alternaria brassicae* and

Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed particularly successfully for combating diseases in fruit and vegetable crops, such as, for example, against Phytophthora species, or combating cereal diseases, such as, for example Pyrenophora species.

In addition, the active compounds according to the invention have a good activity for example against *Erisyphe graminis, Cochliobolus sativus, Leptosphaeria nodorum, Pseudocercosporella herpotrichoides* and Fusarium species in cereals, against *Pyricularia oryzae* and *Pellicularia sasakii* in rice, and a broad in-vitro activity.

Depending on their particular physical and/or chemical properties, the active compounds can be converted into the customary formulations, such as solutions, emulsions, suspensions, powders, foams, pastes, granules, aerosols, very fine capsules in polymeric substances and in coating compositions for seed, and ULV cold and warm mist formulations.

These formulations are produced in a known manner, for example by mixing the active compounds with extenders, that is liquid solvents, liquefied gases under pressure, and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide or dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives my be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used in the form of a mixture with known fungicides, bactericides, acaricides, nematicides or insecticides, for example to broaden the spectrum of action or to prevent resistance build-up. In many cases, synergistic effects are obtained, that is to say the activity of the mixture exceeds the activity of the individual components.

Particularly advantageous components in mixtures are, for example, the following compounds:

Fungicides:

2-aminobutane-2-anilino-4-methyl-6-cyclopropylpyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl) benzamide; (E)-2-methoxyimino-N-methyl-2-(2-phenoxyphenyl)acetamide; 8-hydroxyquinolinesulphate; methyl (E)-2-{2-[6-(2-cyano-phenoxy)pyrimidin- 4-yloxy]phenyl}-3-methoxyacrylate; methyl (E)-methoximino [alpha-(O-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulfide, captarol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazole, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fenitin hydroxide, ferbam, ferimzone, fluazinam, fludioxonil, fluoromide, fluquinconazole, flusilazole, flusulfamide, flutolanil, flutriafol, folpet, fosetylaluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxine, perfurazoat, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram Bactericides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:

abamectin, acephate, acrinathrin, alanycarb, aldicarb, alphamethrin, amitraz, avermectin, AZ 60541, azadirachtin, azinphos A, azinphos M, azocyclotin, Bacillus thuringiensis, 4-bromo-2-(4-chlorphenyl)-1-(ethoxymethyl)-5-(trifluoromethyl)-1H-pyrrole-3-carbonitrile, bendiocarb, benfuracarb, bensultap, betacyluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, chloethocarb, chlorethoxyfos, chlorethoxyfos, chlorfenvinphos, chlorfluazuron, chlormephos, N-[(6-chloro-3-pyridinyl)-methyl]-N'-cyano-N-methylethanimideamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazin, deltamethrin, demeton M, demeton S, deaneton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isopenphos, isoprocarb, isoxathion, ivermecetin, lamda-cyhalothrin, lurehuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos, M, primiphos A, profenofos, profenophos, promecarb, propaphos, propoxur, prothiofos, prothiophos, prothoate, pymetrozin, pyrachlophos, pyraclofos, pyraclophos, pyridaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, thrichlorfon, triflumuron, trimethacarb, vamidothion, XMC, xylylcarb, YI 5301/5302, zetamethrin.

A mixtures with other known active compounds, such as herbicides, or with fertilizers and growth regulators, is also possible.

The active compounds can be used as such, in the form of their formulations or in the use forms prepared therefrom, such as ready-to-use solutions, suspensions, "Spritz" (wettable) powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method, or to inject the active compound preparation or the active compound itself into the soil. The seed of the plants can also be treated.

In the treatment of parts of plants, the active compound concentrations in the use forms can be varied within a substantial range:

In general, they are between 1 and 0.0001% by weight, preferably between 0.5 and 0.001% by weight.

In treatment of seed, amounts of active compound of 0.001 to 50 g, preferably 0.01 to 10 g, are generally required per kilogram of seed.

In the treatment of the soil, concentrations of active compound of 0.00001 to 0.1% by weight, preferably 0.0001 to 0.02% by weight, are required at the site of action.

Preparation Examples

Example 1

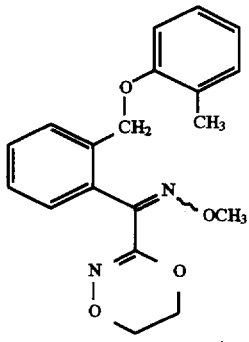

1.8 g (25 mmol) of hydroxylamine hydrochloride are introduced into 20 ml of methanol at 20° C., and a solution of 3.3 g of potassium hydroxide (86%) in 20 ml of methanol is added slowly. 4.0 g (12.8 mmol) of methyl α-methoximino-α-[2-(2-methyl-phenoxy-methyl)-phenyl] acetate are subsequently added in portions, and the reaction mixture is then stirred at 40° C. until the reaction has ended (thin-layer chromatography). First, 1.7 g (12.8 mmol) of potassium carbonate followed by 10.8 g (59 mmol) of 1,2-dibromo-ethane are then added to the reaction mixture. The mixture is then stirred for 12 hours at 65° C. and subsequently cooled to 20° C. and filtered. The filtrate is concentrated under a water pump vacuum, and the residue is purified by column chromatography on silica gel (toluene/acetone, 9:1 by volume).

1.4 g (33% of theory) of 3-{α-methoximino-α-[2-(2-methylphenoxy-methyl)-phenyl]-methyl}-5,6-dihydro-1,4,2-dioxazine are obtained.

melting point: 110° C.

Other examples of the compounds of the formula (I) which can be prepared analogously to Example 1 and following the general description of the preparation processes according to the invention are those listed in Table 1 below.

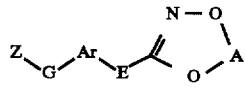

(I)

TABLE 1

Examples of the compounds of the formula (I)

| Ex. No. | Z | G | Ar | E | A | Physical data |
|---|---|---|---|---|---|---|
| 2 | phenyl | H₃C-C(=N-O-CH₂-) | phenyl | CH₃O-N=C< | CH₂CH₂ | 1H-NMR: 2,25; 3,95; 4,05–4,51; 5,15; 7,0–7,68 ppm |
| 3 | 3-methylphenyl | H₃C-C(=N-O-CH₂-) | phenyl | CH₃O-N=C< | CH₂CH₂ | 1H-NMR: 2,23; 2,25; 3,98; 4,1–4,52; 7,05–7,55 ppm |
| 4 | 4-pyridyl-thiadiazolyl | O | phenyl | CH₃O-CH=C< | CH₂CH₂ | |
| 5 | 3-pyridyl-thiadiazolyl | O | phenyl | CH₃O-CH=C< | CH₂CH₂ | |
| 6 | thienyl-thiadiazolyl | O | phenyl | CH₃O-CH=C< | CH₂CH₂ | |
| 7 | phenyl-thiadiazolyl | O | phenyl | CH₃O-CH=C< | CH₂CH₂ | |

TABLE 1-continued

Examples of the compounds of the formula (I)

| Ex. No. | Z | G | Ar | E | A | Physical data |
|---|---|---|---|---|---|---|
| 8 | 2-cyano-phenoxymethyl-1,3,4-thiadiazole | O | phenyl | CH₃O—CH=C< | CH₂CH₂ | |
| 9 | phenylthiomethyl-1,3,4-thiadiazole | O | phenyl | CH₃O—CH=C< | CH₂CH₂ | |
| 10 | 4,6-dimethylpyridin-2-yl-1,3,4-thiadiazole | O | phenyl | CH₃O—CH=C< | CH₂CH₂ | |
| 11 | pyridin-4-yl-1,3,4-thiadiazole | O | phenyl | CH₃O—N=C< | CH₂CH₂ | Fp.: 138° C. |
| 12 | pyridin-3-yl-1,3,4-thiadiazole | O | phenyl | CH₃O—N=C< | CH₂CH₂ | Fp.: 65° C. |

TABLE 1-continued
Examples of the compounds of the formula (I)
| Ex. No. | Z | G | Ar | E | A | Physical data |
|---|---|---|---|---|---|---|
| 13 | 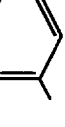 | O | 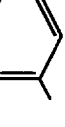 | $CH_3O-N=C<$ | $CH_2CH_2$ | (amorph) $^1$H-NMR: (CDCl$_3$) δ=3,75(s,3H) |
| 14 | 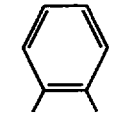 | O | 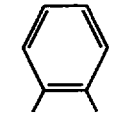 | $CH_3O-N=C<$ | $CH_2CH_2$ | Fp.: 70° C. |
| 15 | 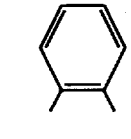 | O | 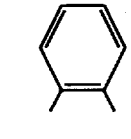 | $CH_3O-N=C<$ | $CH_2CH_2$ | Oil $^1$H-NMR (CDCl$_3$) δ=3,80(s,3H) |
| 16 | 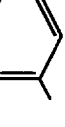 | $SO_2CH_2$ |  | $CH_3O-N=C<$ | $CH_2CH_2$ | |
| 17 | 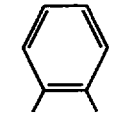 | $-OCH_2-$ | 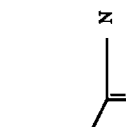 | $CH_3O-N=C<$ | $CH_2CH_2$ | |
| 18 | 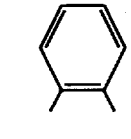 | $-OCH_2-$ | 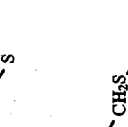 | $CH_3O-N=C<$ | $CH_2CH_2$ | amorph $^1$H-NMR: 1,55; 3,97; 4,16; 4,48; 5,03; 7,08–7,51 ppm |

TABLE 1-continued

Examples of the compounds of the formula (I)

| Ex. No. | Z | G | Ar | E | A | Physical data |
|---|---|---|---|---|---|---|
| 19 | 3,5-dimethylphenyl (H₃C, CH₃) | —OCH₂— | phenyl | CH₃O—N=C< | CH₂CH₂ | m.p.: 129° C. |
| 20 | 2,4-dimethylphenyl (CH₃, CH₃) | —OCH₂— | phenyl | CH₃O—N=C< | CH₂CH₂ | (amorph) 1H-NMR: 2,24; 2,28; 3,99; 4,15; 4,46; 4,98; 6,62–7,59 ppm |
| 21 | 3-chloro-4-methylphenyl (H₃C, Cl) | —OCH₂— | phenyl | CH₃O—N=C< | CH₂CH₂ | Fp.: 123° C. |
| 22 | 2-chlorophenyl (Cl) | —OCH₂— | phenyl | CH₃O—N=C< | CH₂CH₂ | |
| 23 | 4-bromophenyl (Br) | —OCH₂— | phenyl | CH₃O—N=C< | CH₂CH₂ | |
| 24 | i-C₃H₇O-phenyl | —OCH₂— | phenyl | CH₃O—N=C< | CH₂CH₂ | |
| 25 | CH₂=CH—CH₂O-(tolyl) | —OCH₂— | phenyl | CH₃O—N=C< | CH₂CH₂ | |

TABLE 1-continued

Examples of the compounds of the formula (I)

| Ex. No. | Z | G | Ar | E | A | Physical data |
|---|---|---|---|---|---|---|
| 26 | 4-Cl-C₆H₄ | —OCH₂— | phenyl | CH₃O—N=C(CH₃)— | CH₂CH₂ | |
| 27 | 2,4-Cl₂-C₆H₃ | —OCH₂— | phenyl | CH₃O—N=C(CH₃)— | CH₂CH₂ | |
| 28 | 3-CH₃-C₆H₄ | O | phenyl | CH₃O—N=C(CH₃)— | CH₂CH₂ | |
| 29 | C₆H₅ | O | pyridyl | CH₃O—N=C(CH₃)— | CH₂CH₂ | |
| 30 | C₆H₅ | O | thienyl | CH₃O—N=C(CH₃)— | CH₂CH₂ | oil |
| 31 | C₆H₅ | NO-C(CH₃)=N-O-CH₂— | phenyl | CH₃O—N=C(CH₃)— | CH₂CH₂ | |
| 32 | 2-CH₃-C₆H₄ | NO-C(CH₃)=N-O-CH₂— | phenyl | CH₃O—N=C(CH₃)— | CH₂CH₂ | |
| 33 | 3-CH₃-C₆H₄ | NO-C(CH₃)=N-O-CH₂— | phenyl | CH₃O—N=C(CH₃)— | CH₂CH₂ | |

TABLE 1-continued

Examples of the compounds of the formula (I)

| Ex. No. | Z | G | Ar | E | A | Physical data |
|---|---|---|---|---|---|---|
| 34 | 4-CH₃-C₆H₄ | NO-N=C(CH₃)-O-CH₂- | C₆H₄ (o) | CH₃O-N=C(CH₃)- | CH₂CH₂ | |
| 35 | 2-Cl-C₆H₄ | NO-N=C(CH₃)-O-CH₂- | C₆H₄ (o) | CH₃O-N=C(CH₃)- | CH₂CH₂ | |
| 36 | 4-Cl-C₆H₄ | NO-N=C(CH₃)-O-CH₂- | C₆H₄ (o) | CH₃O-N=C(CH₃)- | CH₂CH₂ | |
| 37 | 3-Cl-C₆H₄ | NO-N=C(CH₃)-O-CH₂- | C₆H₄ (o) | CH₃O-N=C(CH₃)- | CH₂CH₂ | |
| 38 | 3,4-Cl₂-C₆H₃ | NO-N=C(CH₃)-O-CH₂- | C₆H₄ (o) | CH₃O-N=C(CH₃)- | CH₂CH₂ | |
| 39 | 3-Br-C₆H₄ | NO-N=C(CH₃)-O-CH₂- | C₆H₄ (o) | CH₃O-N=C(CH₃)- | CH₂CH₂ | |
| 40 | 3,4-(CH₃O)₂-C₆H₃ | NO-N=C(CH₃)-O-CH₂- | C₆H₄ (o) | CH₃O-N=C(CH₃)- | CH₂CH₂ | |
| 41 | 4-CH₃O-C₆H₄ | NO-N=C(CH₃)-O-CH₂- | C₆H₄ (o) | CH₃O-N=C(CH₃)- | CH₂CH₂ | |

TABLE 1-continued
Examples of the compounds of the formula (I)
| Ex. No. | Z | G | Ar | E | A | Physical data |
|---|---|---|---|---|---|---|
| 42 | 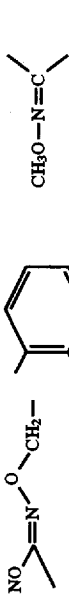 |  |  | CH₃O—N=C | CH₂CH₂ | |
| 43 | 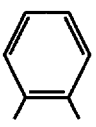 | 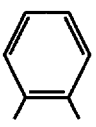 |  | CH₃O—N=C | CH₂CH₂ | |
| 44 |  |  |  | CH₃O—N=C | CH₂CH₂ | |
| 45 |  |  |  | CH₃O—N=C | CH₂CH₂ | |
| 46 |  |  |  | CH₃O—N=C | CH₂CH₂ | |
| 47 |  |  |  | CH₃O—N=C | CH₂CH₂ | |
| 48 |  |  |  | CH₃O—N=C | CH₂CH₂ | |
| 49 |  |  |  | CH₃O—N=C | CH₂CH₂ | |

TABLE 1-continued

Examples of the compounds of the formula (I)

| Ex. No. | Z | G | Ar | E | A | Physical data |
|---|---|---|---|---|---|---|
| 50 | 2-methylpyridinyl | H₃C–C(=N–O–CH₂–) | o-tolyl | CH₃O–N=C | CH₂CH₂ | |
| 51 | 3-(trifluoromethyl)phenyl | H₃C–C(=N–O–CH₂–) | o-tolyl | CH₃O–N=C | CH₂CH₂ | ¹H-NMR (CDCl₃, δ): 2,26(3H); 3,96(3H); 4,1–4,2(2H); 4,4–4,5(2H); 5,204(2H); 7,0–8,0(8H) ppm |
| 52 | 2-cyanophenyl pyrimidinyloxy | O | o-tolyl | CH₃O–N=C | CH₂CH₂ | |
| 53 | 2-(OCHF₂)phenyl pyrimidinyloxy | O | o-tolyl | CH₃O–CH=C | CH₂CH₂ | |
| 54 | 2-methylphenyl | –OCH₂– | 2-F, 6-(E) phenyl (G) | CH₃O–N=C | CH₂CH₂ | ¹H-NMR (CDCl₃, δ): 2,30(3H); 3,98(3H); 4,1–4,2(2H); 4,4–4,5(2H); 4,97(2H); 6,4–7,4(7H) ppm |
| 55 | 3-(trifluoromethyl)phenyl | CH₃\ \–C=N–O–CH₂– | thienyl (G)(E) | CH₃O–N=C | CH₂CH₂ | ¹H-NMR (CDCl₃, δ): 2,25(3H); 4,0(3H); 4,1–4,2(2H); 4,4–4,5(2H); 5,176(2H); 7,114–7,131 (1H); 7,44–7,45(1H); 7,4–8,0(4H) ppm |

TABLE 1-continued

Examples of the compounds of the formula (I)

| Ex. No. | Z | G | Ar | E | A | Physical data |
|---|---|---|---|---|---|---|
| 56 | H₃CO–C(=N)–S–N=C(CH₃)– | –CH₂O– | phenyl | CH₃O–N=C(CH₃)– | CH₂CH₂ | oil |
| 57 | 2-Cl-C₆H₄-CH₂-S-C(=N-S-)(N=C(CH₃)₂) | –O– | phenyl | CH₃O–N=C(CH₃)– | CH₂CH₂ | (amorph) ¹H-NMR (CDCl₃) δ=3.80(s,3H) |
| 58 | 2-CH₃-C₆H₄ | –CH₂O– | phenyl | CH₃O–N=C(CH₃)– | CH₂CH₂ | m.p.: 142° C. |
| 59 | 2,4-(CH₃)₂-C₆H₃ | –CH₂O– | phenyl | CH₃O–N=C(CH₃)– | CH₂CH₂ | oil δ=3.95(s,3H) |
| 60 | 4-CH₃-6-Cl-pyrimidin-2-yl | –O– | phenyl | CH₃O–N=C(CH₃)– | CH₂CH₂ | m.p. 106° C. |
| 61 | 2-CN-C₆H₄-O-C(CH₃)=CH-pyrimidinyl | –O– | phenyl | CH₃O–N=C(CH₃)– | CH₂CH₂ | m.p.: 82° C. |

TABLE 1-continued

Examples of the compounds of the formula (I)

| Ex. No. | Z | G | Ar | E | A | Physical data |
|---|---|---|---|---|---|---|
| 62 | (thiophene with CH₃ and C(CH₃)=N-N=C(CH₃)-S- linkage) | —O— | (phenyl, o-substituted) | CH₃O—N=C(CH₃)— | CH₂CH₂ | oil ¹H-NMR (CDCl₃) δ=3,80(s,3H) |
| 63 | 2,4-dimethylphenyl (H₃C-, CH₃-) | —CH₂O— | (phenyl, o-substituted) | CH₃O—N=C(CH₃)— | CH₂CH₂ | m.p.: 123° C. |
| 64 | 2,3-dimethylphenyl (CH₃, CH₃) | —OCH₂— | (phenyl, o-substituted) | CH₃O—N=C(CH₃)— | CH₂CH₂ | m.p.: 75° C. |
| 65 | 3-chloro-5-methylphenyl (Cl, H₃C) | —OCH₂— | (phenyl, o-substituted) | CH₃O—N=C(CH₃)— | CH₂CH₂ | m.p.: 119° C. |
| 66 | 2-methoxyphenyl (OCH₃) | —OCH₂— | (phenyl, o-substituted) | CH₃O—N=C(CH₃)— | CH₂CH₂ | m.p.: 83° C. |
| 67 | 3-methylphenyl (H₃C) | —OCH₂— | (phenyl, o-substituted) | CH₃O—N=C(CH₃)— | CH₂CH₂ | (amorph) ¹H-NMR: 3,98; 4,15; 4,47; 4,98; 6,80; 7,55 ppm |
| 68 | 4-methylphenyl (H₃C) | —OCH₂— | (phenyl, o-substituted) | CH₃O—N=C(CH₃)— | CH₂CH₂ | (amorph) ¹H-NMR: 2,27; 3,97; 4,14; 4,47; 4,96; 6,18–7,53 ppm |
| 69 | 2-(difluoromethoxy)phenyl (OCHF₂) | —OCH₂— | (phenyl, o-substituted) | CH₃O—N=C(CH₃)— | CH₂CH₂ | (amorph) ¹H-NMR: 3,95; 4,15; 4,48; 5,07; 6,92–7,54 ppm |

TABLE 1-continued

Examples of the compounds of the formula (I)

| Ex. No. | Z | G | Ar | E | A | Physical data |
|---|---|---|---|---|---|---|
| 70 | 2-Br-phenyl | —OCH$_2$— | phenyl | CH$_3$O—N=C | CH$_2$CH$_2$ | m.p.: 131° C. |
| 71 | 4-CH$_3$-phenyl | —O— | phenyl | CH$_3$O—N=C | CH$_2$CH$_2$ | m.p.: 95° C. |
| 72 | 3-CH$_3$-phenyl | —O— | thienyl | CH$_3$O—N=C | CH$_2$CH$_2$ | oil |
| 73 | 4-CH$_3$-phenyl | —O— | thienyl | CH$_3$O—N=C | CH$_2$CH$_2$ | m.p.: 119° C. |
| 74 | 4-CH$_3$O-phenyl | —O— | thienyl | CH$_3$O—N=C | CH$_2$CH$_2$ | oil |
| 75 | 3-CF$_3$-phenyl | —O— | thienyl | CH$_3$O—N=C | CH$_2$CH$_2$ | oil |
| 76 | 3-CF$_3$-phenyl | —O— | phenyl | CH$_3$O—N=C | CH$_2$CH$_2$ | (amorph) |

TABLE 1-continued
Examples of the compounds of the formula (I)
| Ex. No. | Z | G | Ar | E | A | Physical data |
|---|---|---|---|---|---|---|
| 77 |  | —O— | 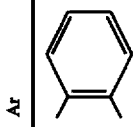 | CH$_3$O—N=C< | CH$_2$CH$_2$ | oil $^1$H-NMR (CDCl$_3$) δ=3.80(s, 3H) |
| 78 | 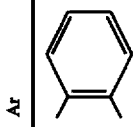 | —CH$_2$S— |  | CH$_3$O—N=C< | CH$_2$CH$_2$ | |
| 79 |  | —SCH$_2$— | 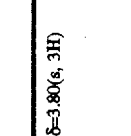 | CH$_3$O—N=C< | CH$_2$CH$_2$ | |
| 80 | 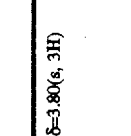 | —CH$_2$S— |  | CH$_3$O—N=C< | CH$_2$CH$_2$ | |
| 81 |  | —SCH$_2$— | 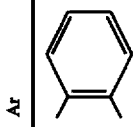 | CH$_3$O—N=C< | CH$_2$CH$_2$ | |

TABLE 1-continued
Examples of the compounds of the formula (I)
| Ex. No. | Z | G | Ar | E | A | Physical data |
|---|---|---|---|---|---|---|
| 82 |  | S | | CH₃O—N=C\ | CH₂CH₂ | |
| 86 | 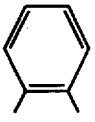 | —O— | | CH₃O—N=C\ | CH₂CH₂ | m.p.: 128° C. |
| 87 | 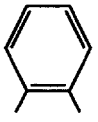 | —O— | | CH₃O—N=C\ | CH₂CH₂ | oil ¹H-NMR (CDCl₃) δ=3.80(s,3H) |
| 88 | 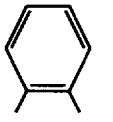 | —O— | | CH₃O—N=C\ | CH₂CH₂ | |
| 89 | 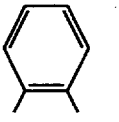 | —O— | | CH₃O—N=C\ | CH₂CH₂ | |

TABLE 1-continued
Examples of the compounds of the formula (I)
| Ex. No. | Z | G | Ar | E | A | Physical data |
|---|---|---|---|---|---|---|
| 90 | 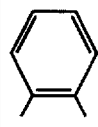 | —O— | 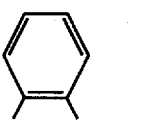 | CH$_3$O—N=C< | CH$_2$CH$_2$ | |
| 91 | 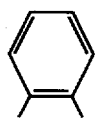 | —O— | 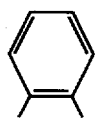 | CH$_3$O—N=C< | CH$_2$CH$_2$ | m.p. 70° C. |
| 92 | 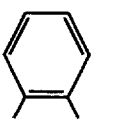 | —O— | 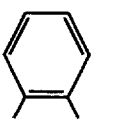 | CH$_3$O—N=C< | CH$_2$CH$_2$ | m.p. 70–73° C. |
| 93 | 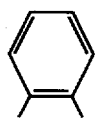 | —O— | 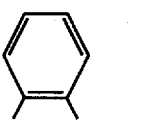 | CH$_3$O—N=C< | CH$_2$CH$_2$ | amorph $^1$H-NMR (CDCl$_3$) δ=3.85(s,3H) |
| 94 | 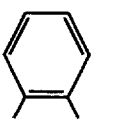 | —O— | 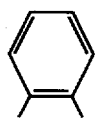 | CH$_3$O—N=C< | CH$_2$CH$_2$ | oil δ=3.85(s, 3H) |

TABLE 1-continued

Examples of the compounds of the formula (I)

| Ex. No. | Z | G | Ar | E | A | Physical data |
|---|---|---|---|---|---|---|
| 95 | Br-C6H4-C(=N-S-C(CH3)=N-) | -O- | phenyl | CH3O-N=C< | CH2CH2 | m.p.: 132° C. |
| 96 | Cl-C6H4-C(=N-S-C(CH3)=N-) | -O- | phenyl | CH3O-N=C< | CH2CH2 | |
| 97 | H3C-C6H4-C(=N-S-C(CH3)=N-) | -O- | phenyl | CH3O-N=C< | CH2CH2 | |
| 98 | pyrimidinyl-O-C6H5 | -O- | phenyl | CH3O-N=C< | CH2CH2 | oil ¹H-NMR (CDCl3) δ=3.80(s,3H) |
| 99 | pyrimidinyl-O-C6H4-CH3 | -O- | phenyl | CH3O-N=C< | CH2CH2 | oil δ=3.80(s, 3H) |

TABLE 1-continued

Examples of the compounds of the formula (I)

| Ex. No. | Z | G | Ar | E | A | Physical data |
|---|---|---|---|---|---|---|
| 100 | 2-Cl-phenoxy pyrimidine | —O— | 2-methylphenyl | CH₃O—N=C< | CH₂CH₂ | amorph ¹H-NMR (CDCl₃) δ=3.80(s, 3H) |
| 101 | 2-F-phenoxy pyrimidine | —O— | 2-methylphenyl | CH₃O—N=C< | CH₂CH₂ | |
| 102 | 3-CH₃-phenoxy pyrimidine | —O— | 2-methylphenyl | CH₃O—N=C< | CH₂CH₂ | amorph δ=3.80(s, 3H) |
| 103 | 3-Cl-phenoxy pyrimidine | —O— | 2-methylphenyl | CH₃O—N=C< | CH₂CH₂ | amorph ¹H-NMR (CDCl₃) δ=3.80(s,3H) |

TABLE 1-continued
Examples of the compounds of the formula (I)
| Ex. No. | Z | G | Ar | E | A | Physical data |
|---|---|---|---|---|---|---|
| 104 |  | —O— | | CH₃O—N=C< | CH₂CH₂ | |
| 105 | 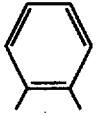 | —O— | | CH₃O—N=C< | CH₂CH₂ | amorph ¹H-NMR (CDCl₃) δ=3.80(s, 3H) |
| 106 |  | —O— | | CH₃O—N=C< | CH₂CH₂ | amorph ¹H-NMR (CDCl₃) δ=3.80(s, 3H) |
| 107 | 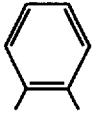 | —O— | | CH₃O—N=C< | CH₂CH₂ | |

TABLE 1-continued
Examples of the compounds of the formula (I)
| Ex. No. | Z | G | Ar | E | A | Physical data |
|---|---|---|---|---|---|---|
| 108 | 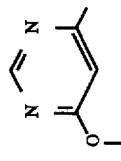 | —O— |  | 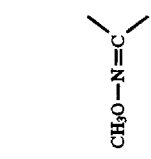 | CH$_2$CH$_2$ | oil $^1$HNMR (CDCl$_3$) δ=3.80(s, 3H) |
| 109 | 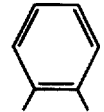 | —O— | 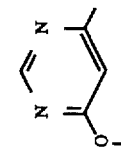 |  | CH$_2$CH$_2$ | |
| 110 | 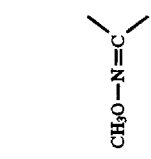 | —O— | 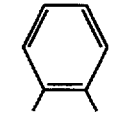 | 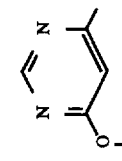 | CH$_2$CH$_2$ | amorph $^1$HNMR (CDCl$_3$) δ=3.80(s, 3H) |

TABLE 1-continued
Examples of the compounds of the formula (I)
| Ex. No. | Z | G | Ar | E | A | Physical data |
|---|---|---|---|---|---|---|
| 111 | 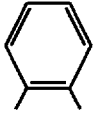 | —O— |  | CH$_3$O—N=C< | CH$_2$CH$_2$ | amorph $^1$HNMR (CDCl$_3$) δ=3.80(s, 3H) |
| 112 | 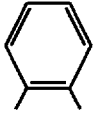 | —O— |  | CH$_3$O—N=C< | CH$_2$CH$_2$ | amorph δ=3.80(s, 3H) |
| 113 | 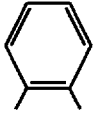 | —O— |  | CH$_3$O—N=C< | CH$_2$CH$_2$ | oil $^1$HNMR (CDCl$_3$) δ=3.80(s, 3H) |
| 114 | 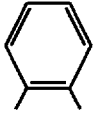 | —O— |  | CH$_3$O—N=C< | CH$_2$CH$_2$ | amorph δ=3.80(s, 3H) |

TABLE 1-continued

Examples of the compounds of the formula (I)

| Ex. No. | Z | G | Ar | E | A | Physical data |
|---|---|---|---|---|---|---|
| 115 | pyrimidine-CH=C(CH₃)- linked to O-phenyl-CF₃ | —O— | o-tolyl | CH₃O—N=C< | CH₂CH₂ | |
| 116 | pyrimidine-CH=C(CH₃)- linked to O-(2,6-dimethylphenyl) | —O— | o-tolyl | CH₃O—N=C< | CH₂CH₂ | amorph ¹HNMR (CDCl₃) δ=3.80(s, 3H) |
| 117 | pyrimidine-CH=C(CH₃)- linked to O-(2,6-dichlorophenyl) | —O— | o-tolyl | CH₃O—N=C< | CH₂CH₂ | |
| 118 | pyrimidine-CH=C(CH₃)- linked to S-phenyl | —O— | o-tolyl | CH₃O—N=C< | CH₂CH₂ | amorph ¹HNMR (CDCl₃) δ=3.80(s, 3H) |

TABLE 1-continued
Examples of the compounds of the formula (I)
| Ex. No. | Z | G | Ar | E | A | Physical data |
|---|---|---|---|---|---|---|
| 119 |  | —O— |  | CH₃O—N=C⟨ | CH₂CH₂ | amorph δ=3.80(s, 3H) |
| 120 | 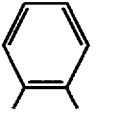 | —O— |  | CH₃O—N=C⟨ | CH₂CH₂ | amorph $^1$HNMR (CDCl₃) δ=3.80(s, 3H) |
| 121 |  | —O— |  | CH₃O—N=C⟨ | CH₂CH₂ | |
| 122 | 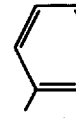 | —O— | 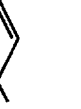 | CH₃O—N=C⟨ | CH₂CH₂ | |

TABLE 1-continued

Examples of the compounds of the formula (I)

| Ex. No. | Z | G | Ar | E | A | Physical data |
|---|---|---|---|---|---|---|
| 123 | (pyrimidine-S-C6H4-Br-4) | —O— | (2-methylphenyl) | CH3O—N=C(CH3)— | CH2CH2 | |
| 124 | (pyrimidine-S-C6H4-Br-2) | —O— | (2-methylphenyl) | CH3O—N=C(CH3)— | CH2CH2 | |
| 125 | (pyrimidine-S-C6H4-CH3-3) | —O— | (2-methylphenyl) | CH3O—N=C(CH3)— | CH2CH2 | |
| 126 | (pyrimidine-S-C6H4-Cl-3) | —O— | (2-methylphenyl) | CH3O—N=C(CH3)— | CH2CH2 | |

TABLE 1-continued

Examples of the compounds of the formula (I)

| Ex. No. | Z | G | Ar | E | A | Physical data |
|---|---|---|---|---|---|---|
| 127 | pyrimidine-CH=C(CH3)-S-C6H4-4-CH3 | —O— | phenyl | CH3O—N=C< | CH2CH2 | |
| 128 | pyrimidine-CH=C(CH3)-S-(2,4-diCH3-C6H3) | —O— | phenyl | CH3O—N=C< | CH2CH2 | |
| 129 | pyrimidine-CH=C(CH3)-S-(2-CN-C6H4) | —O— | phenyl | CH3O—N=C< | CH2CH2 | |
| 130 | pyrimidine-CH=C(CH3)-O-naphthyl | —O— | phenyl | CH3O—N=C< | CH2CH2 | amorph |

TABLE 1-continued

Examples of the compounds of the formula (I)

| Ex. No. | Z | G | Ar | E | A | Physical data |
|---|---|---|---|---|---|---|
| 131 | naphthalen-2-yl with pyrimidinyl-methyl group | —O— | o-tolyl | CH₃O—N=C(CH₃) | CH₂CH₂ | |
| 132 | pyridin-2-ylthio with pyrimidinyl-methyl group | —O— | o-tolyl | CH₃O—N=C(CH₃) | CH₂CH₂ | amorph ¹H-NMR (CDCl₃) δ=3.85(s,3H) |
| 133 | pyridin-3-ylthio with pyrimidinyl-methyl group | —O— | o-tolyl | CH₃O—N=C(CH₃) | CH₂CH₂ | |
| 134 | pyridin-4-ylthio with pyrimidinyl-methyl group | —O— | o-tolyl | CH₃O—N=C(CH₃) | CH₂CH₂ | |

TABLE 1-continued

Examples of the compounds of the formula (I)

| Ex. No. | Z | G | Ar | E | A | Physical data |
|---|---|---|---|---|---|---|
| 135 | pyrimidinyl-O-pyridinyl | —O— | phenyl (2-Me) | CH₃O—N=C< | CH₂CH₂ | amorph ¹HNMR (CDCl₃) δ=3.85(s, 3H) |
| 136 | 4-methylphenyl | —CH₂O— | phenyl (2-Me) | CH₃O—N=C< | CH₂CH₂ | |
| 137 | 3-methylphenyl | —CH₂O— | phenyl (2-Me) | CH₃O—N=C< | CH₂CH₂ | |
| 138 | 3-methylphenyl | —CH₂O— | phenyl (2-Me) | CH₃O—N=C< | CH₂CH₂ | |
| 139 | 2,6-dimethylphenyl | —CH₂O— | phenyl (2-Me) | CH₃O—N=C< | CH₂CH₂ | m.p.: 146° C. |
| 140 | 2,6-dimethylphenyl | —CH₂O— | phenyl (2-Me) | CH₃O—N=C< | CH₂CH₂ | |
| 141 | 3,5-dimethylphenyl | —CH₂O— | phenyl (2-Me) | CH₃O—N=C< | CH₂CH₂ | |

TABLE 1-continued

Examples of the compounds of the formula (I)

| Ex. No. | Z | G | Ar | E | A | Physical data |
|---|---|---|---|---|---|---|
| 142 | 2-Cl-C₆H₄ | —CH₂O— | C₆H₄ | CH₃O—N=C< | CH₂CH₂ | |
| 143 | 2-F-C₆H₄ | —CH₂O— | C₆H₄ | CH₃O—N=C< | CH₂CH₂ | |
| 144 | 3-Cl-C₆H₄ | —CH₂O— | C₆H₄ | CH₃O—N=C< | CH₂CH₂ | |
| 145 | 4-Cl-C₆H₄ | —CH₂O— | C₆H₄ | CH₃O—N=C< | CH₂CH₂ | |
| 146 | 2,4-Cl₂-C₆H₃ | —CH₂O— | C₆H₄ | CH₃O—N=C< | CH₂CH₂ | |
| 147 | 4-F-C₆H₄ | —CH₂O— | C₆H₄ | CH₃O—N=C< | CH₂CH₂ | |
| 148 | 2,4-F₂-C₆H₃ | —CH₂O— | C₆H₄ | CH₃O—N=C< | CH₂CH₂ | |
| 149 | 2,4-(CH₃)₂-C₆H₃ | —CH₂O— | C₆H₄ | CH₃O—N=C< | CH₂CH₂ | |

TABLE 1-continued

Examples of the compounds of the formula (I)

| Ex. No. | Z | G | Ar | E | A | Physical data |
|---|---|---|---|---|---|---|
| 150 | 3-Cl, 4-CH₃ (Cl, Cl on ring with CH₃) | —CH₂O— | phenyl | CH₃O—N=C< | CH₂CH₂ | |
| 151 | 2-Cl, 4-Cl | —CH₂O— | phenyl | CH₃O—N=C< | CH₂CH₂ | |
| 152 | 2-Cl, 6-Cl | —CH₂O— | phenyl | CH₃O—N=C< | CH₂CH₂ | |
| 153 | 2-CF₃ | —CH₂O— | phenyl | CH₃O—N=C< | CH₂CH₂ | |
| 154 | 2-OCH₃ | —CH₂O— | phenyl | CH₃O—N=C< | CH₂CH₂ | |
| 155 | 1-naphthyl | —CH₂O— | phenyl | CH₃O—N=C< | CH₂CH₂ | |
| 156 | 2-naphthyl | —CH₂O— | phenyl | CH₃O—N=C< | CH₂CH₂ | |
| 157 | 2-Cl, 4-Cl, CH₃ | — | thiazole | CH₃O—CH=C(—N(CH₃)—) | CH₂CH₂ | |

TABLE 1-continued

Examples of the compounds of the formula (I)

| Ex. No. | Z | G | Ar | E | A | Physical data |
|---|---|---|---|---|---|---|
| 158 | 4-H₃C-C₆H₄ | — | thiazol-2-yl (H) | CH₃O—CH=C—N—CH₃ | CH₂CH₂ | |
| 159 | 4-Br-C₆H₄ | — | thiazol-2-yl (H) | CH₃O—CH=C—N—CH₃ | CH₂CH₂ | |
| 160 | 4-Cl-C₆H₄ | — | thiazol-2-yl (H) | CH₃O—CH=C—N—CH₃ | CH₂CH₂ | |
| 161 | C₆H₅ | — | thiazol-2-yl (H) | CH₃O—CH=C—N—CH₃ | CH₂CH₂ | |
| 162 | 4-Cl-C₆H₄ | — | thiazol-2-yl (Br) | CH₃O—CH=C—N—CH₃ | CH₂CH₂ | |
| 163 | 4-Br-C₆H₄ | — | thiazol-2-yl (Br) | CH₃O—CH=C—N—CH₃ | CH₂CH₂ | |
| 164 | 3-F₃C-C₆H₄ | — | thiazol-2-yl (Br) | CH₃O—CH=C—N—CH₃ | CH₂CH₂ | |
| 165 | 3-Br-C₆H₄ | — | thiazol-2-yl (Cl) | CH₃O—CH=C—N—CH₃ | CH₂CH₂ | |

TABLE 1-continued
Examples of the compounds of the formula (I)
| Ex. No. | Z | G | Ar | E | A | Physical data |
|---|---|---|---|---|---|---|
| 166 | 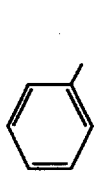 | — | 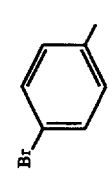 | CH₃O—CH=C—N—CH₃ | CH₂CH₂ | |
| 167 | 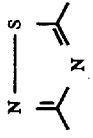 | — | 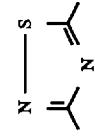 | CH₃O—CH=C—N—CH₃ | CH₂CH₂ | |
| 168 | 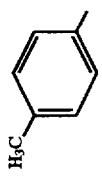 | — |  | CH₃O—CH=C—N—CH₃ | CH₂CH₂ | |
| 169 | 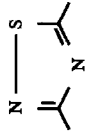 | — | 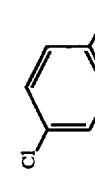 | CH₃O—CH=C—N—CH₃ | CH₂CH₂ | |
| 170 |  | — | 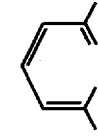 | CH₃O—CH=C—N—CH₃ | CH₂CH₂ | |
| 171 | 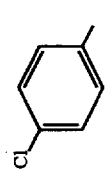 | — |  | CH₃O—CH=C—N—CH₃ | CH₂CH₂ | |
| 172 | 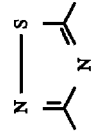 | — | 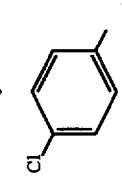 | CH₃O—CH=C—N—CH₃ | CH₂CH₂ | |
| 173 |  | — | 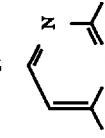 | CH₃O—CH=C—N—CH₃ | CH₂CH₂ | |

TABLE 1-continued
Examples of the compounds of the formula (I)
| Ex. No. | Z | G | Ar | E | A | Physical data |
|---|---|---|---|---|---|---|
| 174 | 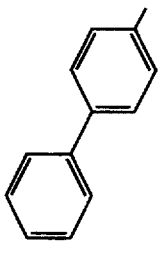 | — |  | CH₃O—CH=C—N—CH₃ | CH₂CH₂ | |
| 175 | 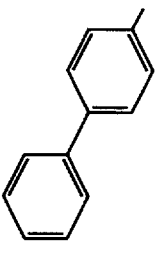 | — |  | CH₃O—CH=C—N—CH₃ | CH₂CH₂ | |
| 176 | 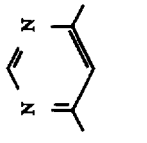 | — |  | CH₃O—CH=C—N—CH₃ | CH₂CH₂ | |
| 177 | 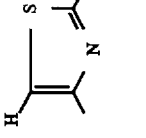 | — |  | CH₃O—CH=C—N—CH₃ | CH₂CH₂ | |
| 178 | 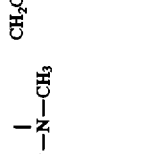 | — |  | CH₃O—CH=C—N—CH₃ | CH₂CH₂ | |
| 179 | 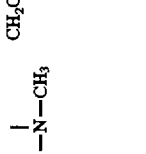 | — | 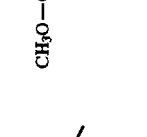 | CH₃O—CH=C—N—CH₃ | CH₂CH₂ | |
| 180 |  | — | 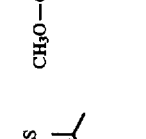 | CH₃O—CH=C—N—CH₃ | CH₂CH₂ | |

TABLE 1-continued

Examples of the compounds of the formula (I)

| Ex. No. | Z | G | Ar | E | A | Physical data |
|---|---|---|---|---|---|---|
| 181 | 4-biphenyl | — | pyrimidine-4,6-diyl (2,6-dimethyl) | CH₃O—CH=C(—N(CH₃))— | CH₂CH₂ | |
| 182 | 3-(phenoxy)phenyl | — | pyridine-2,6-diyl (with methyl) | CH₃O—CH=C(—N(CH₃))— | CH₂CH₂ | |
| 183 | 2-isopropylphenyl | —OCH₂— | phenyl | CH₃O—N=C(CH₃)— | CH₂CH₂ | (amorph) ¹H-NMR: 1,23; 1,26; 3,39–3,46; 4,0; 4,15; 4,48; 5,0; 6,8–7,6 ppm |
| 184 | 1-naphthyl | —OCH₂— | phenyl | CH₃O—N=C(CH₃)— | CH₂CH₂ | m.p.: 115° C. |
| 185 | 2-fluorophenyl | —OCH₂— | phenyl | CH₃O—N=C(CH₃)— | CH₂CH₂ | m.p.: 103° C. |
| 186 | 2-ethyl-4-methylphenyl | —OCH₂— | phenyl | CH₃O—N=C(CH₃)— | CH₂CH₂ | m.p.: 62° C. |
| 187 | phenyl | — | pyridine-2,6-diyl (with methyl) | CH₃O—CH=C(—N(CH₃))— | CH₂CH₂ | |

TABLE 1-continued

Examples of the compounds of the formula (I)

| Ex. No. | Z | G | Ar | E | A | Physical data |
|---|---|---|---|---|---|---|
| 188 | 3-CF$_3$-phenyl | — | 2,6-dimethylpyridin-yl | CH$_3$O—CH=C(—N(CH$_3$)—)— | CH$_2$CH$_2$ | |
| 189 | 2,3-dichlorophenyl | — | 2,6-dimethylpyridin-yl | CH$_3$O—CH=C(—N(CH$_3$)—)— | CH$_2$CH$_2$ | |
| 190 | 4-CH$_3$-phenyl | — | 2,6-dimethylpyridin-yl | CH$_3$O—CH=C(—N(CH$_3$)—)— | CH$_2$CH$_2$ | |
| 191 | 4-Br-phenyl | — | 2,6-dimethylpyridin-yl | CH$_3$O—CH=C(—N(CH$_3$)—)— | CH$_2$CH$_2$ | |
| 192 | 2-Br-3-CH$_3$-phenyl | — | 2,6-dimethylpyridin-yl | CH$_3$O—CH=C(—N(CH$_3$)—)— | CH$_2$CH$_2$ | |
| 193 | 3-CF$_3$-phenyl | —O— | pyridinyl (E,G) 4-methyl | CH$_3$O—N=C(CH$_3$)— | CH$_2$CH$_2$ | m.p.: 118° C. |
| 194 | 3-Br-phenyl | —O— | pyridinyl (E,G) 4-methyl | CH$_3$O—N=C(CH$_3$)— | CH$_2$CH$_2$ | amorph |
| 195 | 3-Cl-phenyl | —O— | pyridinyl (E,G) 4-methyl | CH$_3$O—N=C(CH$_3$)— | CH$_2$CH$_2$ | |

TABLE 1-continued

Examples of the compounds of the formula (I)

| Ex. No. | Z | G | Ar | E | A | Physical data |
|---|---|---|---|---|---|---|
| 196 | H₅C₂CH₂O-phenyl (3-substituted) | —O— | pyridine (G at 2, E at 3, CH₃ at 4) | CH₃O—N=C< | CH₂CH₂ | |
| 197 | 4-F, 3-CH₃-phenyl | —OCH₂— | phenyl | CH₃O—N=C< | CH₂CH₂ | ¹H-NMR: 3,98; 4,16; 4,49; 5,09; 6,82–7,56 ppm |
| 198 | 2-Br, 3-CH₃-phenyl | —OCH₂— | phenyl | CH₃O—N=C< | CH₂CH₂ | ¹H-NMR: 2,29; 3,95; 4,15; 4,47; 4,17; 6,92–7,82 ppm |
| 199 | 2,6-(CH₃)₂-phenyl | —OCH₂— | phenyl | CH₃O—N=C< | CH₂CH₂ | ¹H-NMR: 2,26; 3,99; 4,19; 4,5; 5,06; 6,67–7,62 ppm |
| 200 | 2-Cl, 4-CH₃-phenyl | —OCH₂— | phenyl | CH₃O—N=C< | CH₂CH₂ | ¹H-NMR: 2,17–2,29; 3,98; 4,14; 4,48; 4,96; 6,5–7,6 ppm |
| 201 | 2,4,6-(CH₃)₃-phenyl | —OCH₂— | phenyl | CH₃O—N=C< | CH₂CH₂ | |
| 202 | 2,3,4,6-(CH₃)₄-phenyl | —OCH₂— | phenyl | CH₃O—N=C< | CH₂CH₂ | |

TABLE 1-continued

Examples of the compounds of the formula (I)

| Ex. No. | Z | G | Ar | E | A | Physical data |
|---|---|---|---|---|---|---|
| 203 | 2,3-dimethylphenyl (CH₃, CH₃) | —OCH₂— | phenyl | CH₃O—N=C | CH₂CH₂ | ¹H-NMR: 2,20; 2,28; 3,97; 4,15; 4,46; 4,98; 6,68–7,58 ppm |
| 204 | 6-methylnaphth-2-yl | —OCH₂— | phenyl | CH₃O—N=C | CH₂CH₂ | |
| 205 | 3'-methylbiphenyl | —OCH₂— | phenyl | CH₃O—N=C | CH₂CH₂ | |
| 206 | 2-allyl-phenyl (CH₂CH=CH₂) | —OCH₂— | phenyl | CH₃O—N=C | CH₂CH₂ | |
| 207 | 2-ethyl-phenyl (C₂H₅) | —OCH₂— | phenyl | CH₃O—N=C | CH₂CH₂ | |
| 208 | 4-isopropyl-2-methyl-phenyl (CH₃, i-C₃H₇) | —OCH₂— | phenyl | CH₃O—N=C | CH₂CH₂ | ¹H-NMR: 1,19; 1,21; 2,25; 2,82; 3,98; 4,15; 4,45; 5,0; 6,66–7,58 ppm |
| 209 | 4-methyl-2-methylthio-phenyl (MeS, H₃C) | —OCH₂— | phenyl | CH₃O—N=C | CH₂CH₂ | ¹H-NMR: 2,34; 2,38; 3,98; 4,15; 4,47; 4,97; 6,73–7,52 ppm |
| 210 | HC≡C—H₂C—O—(3-methylphenyl) | —OCH₂— | phenyl | CH₃O—N=C | CH₂CH₂ | |

TABLE 1-continued

Examples of the compounds of the formula (I)

| Ex. No. | Z | G | Ar | E | A | Physical data |
|---|---|---|---|---|---|---|
| 211 | 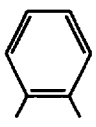 (CF₃O-phenyl) | —OCH₂— | phenyl | CH₃O—N=C< | CH₂CH₂ | |
| 212 | 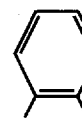 (i-C₃H₇O-phenyl) | —OCH₂— | phenyl | CH₃O—N=C< | CH₂CH₂ | |
| 213 | 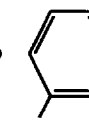 (CH₂=CHCH₂O-, CH₃-phenyl) | —OCH₂— | phenyl | CH₃O—N=C< | CH₂CH₂ | |
| 214 | 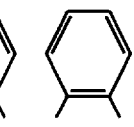 (H₃CON=HC-phenyl) | —OCH₂— | phenyl | CH₃O—N=C< | CH₂CH₂ | amorph ¹H-NMR: 3,97; 4,13; 4,45; 5,03; 6,86–8,50 ppm |
| 215 |  (H₃CON=HC-, CH₃-phenyl) | —OCH₂— | phenyl | CH₃O—N=C< | CH₂CH₂ | ¹H-NMR: 3,94; 3,97; 4,15; 4,47; 5,02; 6,90–8,0 ppm |
| 216 | 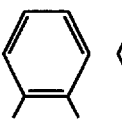 (H₃CON=HC-, CH₃-phenyl) | —OCH₂— | phenyl | CH₃O—N=C< | CH₂CH₂ | ¹H-NMR: 3,98; 4,15; 4,47; 5,01; 6,92–8,02 ppm |
| 217 | 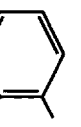 (H₃CON=HC-, CH₃-phenyl) | —OCH₂— | phenyl | CH₃O—N=C< | CH₂CH₂ | |
| 218 | 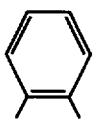 (H₃CO-pyrimidine) | O | phenyl | CH₃O—N=C< | CH₂CH₂ | m.p.: 133° C. |

TABLE 1-continued
Examples of the compounds of the formula (I)
| Ex. No. | Z | G | Ar | E | A | Physical data |
|---|---|---|---|---|---|---|
| 219 |  | O |  | CH₃O—N=C< | CH₂CH₂ | amorph ¹H-NMR (CDCl₃) δ=3,15(s,3H) |
| 220 |  | O |  | CH₃O—N=C< | CH₂CH₂ | amorph δ=3,80(s,3H) |
| 221 |  | O |  | CH₃O—N=C< | CH₂CH₂ | m.p.: >200° C. |
| 222 |  | —OCH₂— |  | CH₃O—N=C< | CH₂CH₂ | amorph ¹H-NMR: 3,97; 4,14; 4,46; 5,0; 6,91–7,54 ppm |
| 223 |  | —OCH₂— |  | CH₃O—N=C< | CH₂CH₂ | amorph ¹H-NMR: 3,97; 4,14; 4,48; 5,03; 7,08–7,51 ppm |

TABLE 1-continued

Examples of the compounds of the formula (I)

| Ex. No. | Z | G | Ar | E | A | Physical data |
|---|---|---|---|---|---|---|
| 224 | OCH₂C₆H₅ (para-subst. phenyl) | O | pyridine with (G) and (E) substituents, CH₃ | CH₃O—N=C< | CH₂CH₂ | amorph |
| 225 | CH₃ (ortho-subst. phenyl) | —OCH₂— | phenyl | CH₃O—N=C< | CH₂ | ¹H-NMR: 2,25; 4,0; 5,0; 5,86; 6,75–7,6 ppm |
| 226 | CH₃ (ortho-subst. phenyl) | —OCH₂— | phenyl | CH₃O—N=C< | CH(CH₃) | |
| 227 | CH₃ (ortho-subst. phenyl) | —OCH₂— | phenyl | CH₃O—N=C< | CH₂CH(CH₃) | ¹H-NMR: 1,4; 2,3; 3,6–4,5; 5,0; 6,8–7,6 ppm |

The compound given as Example 60 Table 1 can be prepared, for example, as follows:

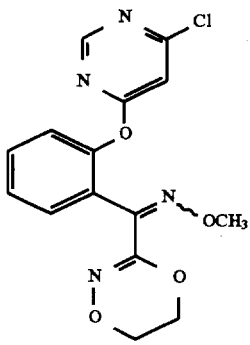

0.3 g (6 mmol) of a 60% strength suspension of sodium hydride in petroleum white oil is added to a mixture of 1.5 g (6 mmol) of 3-[α-methoximino-α-(2-hydroxy-phenyl)m-ethyl]-5,6-dihydro-1,4,2-dioxazine, 0.9 g (6 mmol) of 4,6-dichloro-pyrimidine and 30 ml of N,N-dimethylformamide, with ice-cooling. After the ice bath has been removed, the reaction mixture is stirred for 15 hours at 20° C. It is then concentrated under an oil-pump vacuum, and the residue is taken up in ethyl acetate, washed with water, dried using sodium sulphate and filtered. The solvent is carefully removed from the filtrate by distillation under a water pump vacuum.

1.9 g (86% of theory) of 3-{α-methoximino-α-[2-(6-chloropyrimidin-4-yl-oxy)-phenyl]-methyl}-5,6-dihydro-1,4,2-dioxazine are obtained as an oily residue.

The compound given as Example 61 in Table 1 can be prepared, for example, as follows:

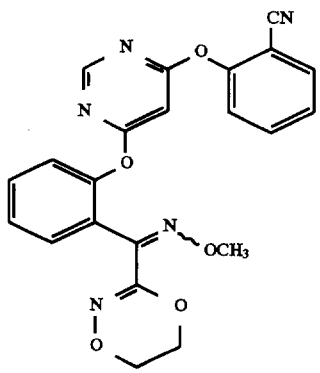

A mixture of 0.3 g (0.9 mmol) of 3-{α-methoximino-α-[2-(6-chloro-pyrimidin-4-yl-oxy)-phenyl]-methyl}-5,6-dihydro-1,4,2-dioxazine, 0.1 g (0.9 mmol) of 2-hydroxybenzonitrile, 0.1 g (0.9 mmol) of potassium carbonate, a spatula-tipful of copper(I) chloride and 5 ml of N,N-dimethyl-formamide is stirred for 15 hours at 100° C. It is then concentrated under an oil-pump vacuum, and the residue is takenup in ethyl acetate, washed with water, dried using sodium sulphate and filtered. The filtrate is concentrated, and the residue is purified column chromatography on silica gel (using hexane/acetone, 7:3 by volume).

0.3 g (81% of theory) of 3-{α-methoximino-α-[2-(6-(2-cyano-phenoxy)-pyrimidin-4-yl-oxy)-phenyl]methyl}-5,6-dihydro-1,4,2-dioxazine of melting point 82° C. is obtained.

The compound given as Example 58 in Table 1 can be prepared, for example, as follows:

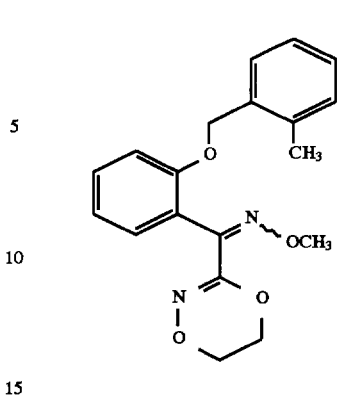

A mixture of 0.5 g (2 mmol) of 3-[α-methoximino-α-(2-hydroxy-phenyl)-methyl]-5,6-dihydro-1,4,2 -dioxazine, 0.3 g (2.2 mmol) of 2-methyl-benzyl chloride, 0.4 g (2.5 mmol) of potassium carbonate and 10 ml of acetonitrile is refluxed for 15 hours. It is then concentrated, and the residue is taken up in methylene chloride, washed with water, dried using sodium sulphate and filtered. The solvent is carefully removed from the filtrate by distillation under a water pump vacuum.

0.4 g (59% of theory) of 3-{α-methoximino-α-[2-(2-methylbenzyloxy)-phenyl]-methyl}-5,6-dihydro-1,4,2-dioxazine of melting point 142° C. is obtained.

Alternatively, the compound which can be obtained in accordance with Example 1 can be prepared, for example, as follows:

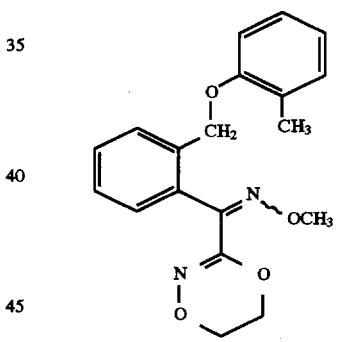

0.75 g (2.4 mmol) of 3-[α-methoximino-α-(2-bromomethylphenyl)-methyl]-5,6-dihydro-1,4,2-dioxazine and 0.70 g (6.4 mmol) of 2-methyl-phenol are dissolved in 15 ml of dimethylformamide, and, after the mixture has been cooled to −10° C., 0.21 g (7.0 mmol) of sodium hydride (80% strength) is added slowly. After the cooling bath has been removed, the reaction mixture is stirred for 14 hours at not more than 25° C. and subsequently poured into approximately twice the volume of water. After shaking with ethyl acetate, the organic phase is separated off, washed with 2N sodium hydroxide solution, dried using sodium sulphate and filtered. The solvent is carefully removed from the filtrate by distillation under reduced pressure.

0.40 g (49% of theory) of 3-{α-methoximino-α-[2-(2-methyl-phenoxy-methyl)-phenyl]-methyl}-5,6-dihydro-1,4, 2-dioxazine is obtained (Refractive index: $n_D^{20}$=1.5705).

The compound given as Example 19 in Table 1 can be prepared, for example, as follows:

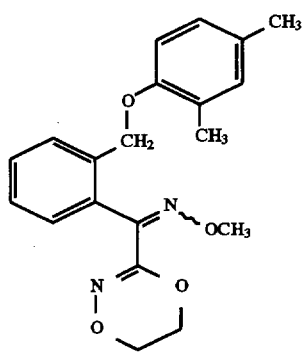

0.20 g (0.56 mmol) of N-(2-hydroxy-ethoxy)-α-methoximino-α-[2-(2,4-dimethyl-phenoxy-methyl)-phenyl]-acetamide is dissolved in 3 ml of chloroform, and 0.25 g (1.76 mmol) of phosphorus(V) oxide is added at 0° C. The reaction mixture is stirred for 1 hour at 20° C. and then for 4 hours under reflux, subsequently poured into approximately twice the volume of water and shaken. After the organic phase has been separated off, the aqueous phase is re-extracted three times with chloroform. The combined organic extracts are dried using magnesiumsulphate, then concentrated and purified by column chromatography (silica gel; toluene/acetone, 10:1).

84 mg (42% of theory) of 3-{α-methoximino-α-[2-(2,4-dimethyl-phenoxy-methyl)-phenyl]-methyl}-5,6-dihydro-1,4,2-dioxazine are obtained.

$^1$H NMR (D$_6$-DMSO, δ): 4.87, 3.84, 4.38, 4.10 ppm.

Starting substances of the formula (IV):

Example (IV-1)

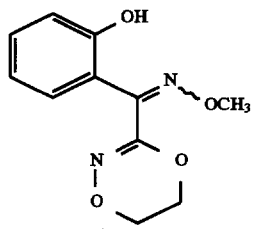

9.0 g (28 mmol) of 3-[α-methoximino-α-(2-tetrahydropyran-2-yl-oxy)-benzyl]-5,6-dihydro-1,4,2-dioxazine and 1.8 g of ion exchanger "Lewatit SPC 108" in 90 ml of methanol are stirred for 15 hours at 20° C. The mixture is then concentrated under a water pump vacuum, and the residue is taken up in methylene chloride and filtered. The filtrate is concentrated under a water pump vacuum, and the residue is purified by column chromatography on silica gel (using hexane/acetone, 7:3 by volume).

The 1st fraction obtained is 0.6 g (9% of theory) of Z-{3-[α-methoximino-α-(2-hydroxy-phenyl)-methyl]-5,6-dihydro-1,4,2-dioxazine} in the form of an amorphous product, and the 2nd fraction is 3.3 g (50% of theory) of E-{3-[α-methoximino-α-(2-hydroxy-phenyl)-methyl]-5,6-dihydro-1,4,2-dioxazine} of melting point 153° C.

Starting substances of the formula (IX):

Example (IX-1)

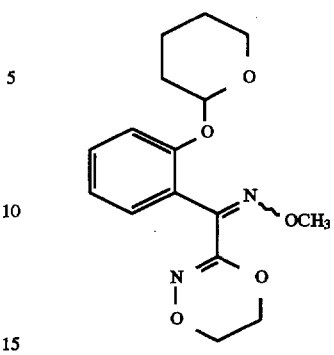

13.9 g (211 mmol) of an 85% strength aqueous potassium hydroxide solution and 17 g (58 mmol) of methyl α-methoximino-α-(2-tetrahydropyran-2-yl-oxy-phenyl)-acetate are added to 6.8 g (98 mmol) of hydroxylamine hydrochloride in 290 ml of methanol, and the mixture is stirred for one hour at 40° C. 7.7 g (56 mmol) of potassium carbonate are then added, and 42.5 g (226 mmol) of 1,2-dibromoethane are added dropwise. The mixture is then refluxed for 15 hours and subsequently concentrated under a water pump vacuum. The residue is taken up in methylene chloride, washed with water, dried using sodium sulphate and filtered. The filtrate is concentrated, and the residue is purified by column chromatography on silica gel (using hexane/acetone, 7:3 by volume).

9.0 g (49% of theory) of 3-[α-methoximino-α-(2-tetrahydropyran-2-yl-oxy)-benzyl]-5,6-dihydro-1,4,2-dioxazine are obtained as an oily product.

Starting substances of the formula (X):

Example (X-1)

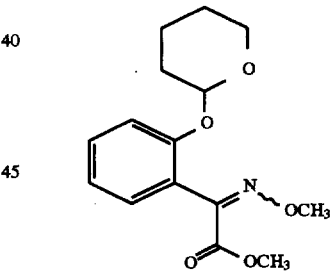

203 g (1.81 mol) of potassium t-butylate are introduced into 2 liters of t-butanol, and 564 g (4.93 mol) of t-butyl nitrite and 411 g (1.64 mol) of methyl 2-tetrahydropyranyloxy-phenyl acetate—dissolved in 500 ml of t-butanol—are added dropwise to this solution. After 90 minutes, 350 g (2.47 mol) of methyl iodide are added dropwise and the mixture is stirred for 15 hours at 20° C. It is then concentrated under a water pump vacuum, and the residue is taken up in methyl t-butyl ether, dried using sodium sulphate and filtered. The residue is brought to crystallization by digestion with diethyl ether and the product is isolated by filtration with suction.

69.3 g (15% of theory) of methyl α-methoximino-α-(2-tetrahydropyran-2-yl-oxy-phenyl)-acetate of melting point 79° C. are obtained.

Starting substances of the formula (XI):

Example (XI-1)

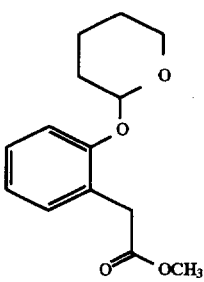

A mixture of 500 g (3.0 mol) of methyl 2-hydroxyphenyl-acetate, 506 g (6.0 mol) of 3,4-dihydro-pyran, a spatula-tipful of p-toluene-sulphonic acid and 2.5 liters of tetrahydrofuran is stirred for 15 hours at 20° C. and then stirred with ice-cold 10% strength aqueous potassium hydroxide solution, sodium sulphate is added, and the mixture is filtered. The solvent is carefully removed from the filtrate by distillation under water pump vacuum.

698 g (99% of theory) of methyl 2-tetrahydropyranyloxyphenyl-acetate are obtained as an oily residue.

Starting substances of the formula (VI):

Example (VI-1)

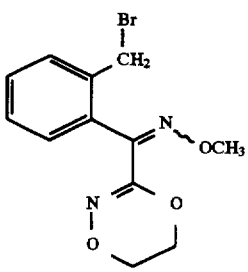

0.50 g (2.13 mmol) of 3-[α-methoximino-α-(2-methylphenyl)-methyl]-5,6-dihydro-1,4,2-dioxazine and 0.57 g (3.2 mmol) of N-bromo-succinimide are introduced into 10 ml of tetrachloromethane and, after 200 mg of azoisobutyronitrile have been added, the mixture is refluxed for 4 hours. After an addition of a further 0.57 g (3.2 mmol) of N-bromo-succinimide, the mixture is refluxed for a further hour. It is subsequently cooled and filtered, the filtrate is concentrated, and the residue is chromatographed (silica gel; toluene/acetone, 10:1).

20 mg (30% of theory) of 3-[α-methoximino-α-(2-bromomethyl-phenyl)-methyl]-5,6-dihydro-1,4,2-dioxazine are obtained.

¹H NMR (CDCl₃, δ): 4.4 ppm.

Starting substances of the formula (XIII):

Example (XIII-1)

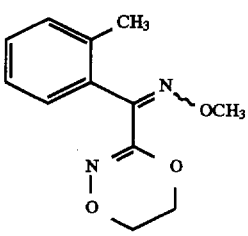

19.6 g (0.283 mol) of hydroxylamine hydrochloride are introduced into 150 ml of methanol, and a solution of 36.9 g (0.565 mol) of potassium hydroxide (86% strength) in 150 ml of methanol is added slowly. 30 g (0.145 mol) of methyl α-methoximino-α-(2-methyl-phenyl)-acetate are then added in portions. The mixture is stirred for 3 hours at 50° C. 20 g (0.145 mol) of potassium carbonate and 122 g (0.65 mol) of 1,2-dibromo-ethane are subsequently added at 20° C., and the reaction mixture is stirred for 17 hours at 65° C. After the mixture has been cooled, it is subjected to filtration with suction, the filtrate is concentrated, and the residue is chromatographed (silica gel; toluene/acetone, 15:1).

15.2 g (45% of theory) of 3-[α-methoximino-α-(2-methylphenyl)-methyl]-5,6-dihydro-1,4,2-dioxazine are obtained.

¹H NMR (CDCl₃, δ): 2.2 ppm.

Starting substances of the formula (XIV):

Example (XIV-1)

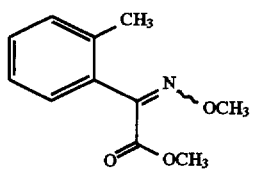

187.5 g (1.673 mol) of potassium t-butylate are dissolved in 1875 ml of t-butanol. 471.5 g (4.57 mol) of t-butyl nitrite and 250 g (1.525 mol) of methyl 2-methyl-phenyl acetate—dissolved in 500 ml of t-butanol—are metered in in such a manner that the internal temperature does not rise above 50° C. The mixture is stirred for 90 minutes at from 20° C. to 30° C. 326.5 g (2.3 mol) of methyl iodide are then added dropwise, and the reaction mixture is stirred for 14 hours at 20° C. The solvent is subsequently distilled off under water pump vacuum, the residue is takenup in 2 liters of water, and the mixture is extracted three times using ethyl acetate. The combined organic phases are dried over sodium sulphate and filtered. The filtrate is concentrated, the residue is taken up in 250 ml of isopropanol, and water is added under reflux until the mixture has turned cloudy.

After the mixture has been cooled to 0° C. and stirred for 60 minutes, the product obtained as crystals is isolated by filtration under suction.

84.5 g (27% of theory) of methyl α-methoximino-α-(2-methyl-phenyl)-acetate of melting point 53° C. are obtained.

¹H NMR (CDCl₃, δ): 2.19 ppm.

Starting substances of the formula (VIII):

101
Example (VIII-1)

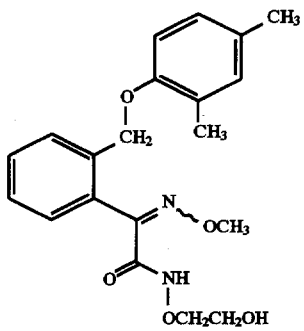

0.8 g (2.36 mmol) of α-methoximino-α-[2-(2,4-dimethylphenoxy-methyl)-phenyl]-acetyl chloride is dissolved in 10 ml of tetrahydrofuran and 0.26 g (2.6 mmol) of triethylamine is added. 0.25 g (2.6 mmol) of 0-(2-hydroxyethyl)-hydroxylamine, dissolved in 10 ml of tetrahydrofuran, is then added dropwise at 0° C. The reaction mixture is stirred for 2 hours at 20° C. and then poured into water and extracted using ethyl acetate. The extraction solution is dried using magnesium sulphate, concentrated and chromatographed (silica gel; toluene/acetone, 10:1).

0.4 g (50% of theory) of N-(2-hydroxy-ethoxy)-α-methoximino-α-[2-(2,4-dimethyl-phenoxy-methyl)-phenyl]-acetamide is obtained.

$^1$H NMR (CDCl$_3$, δ): 3.65; 3.90; 9.15 ppm.

Starting substances of the formula (XV):

Example (XV-1)

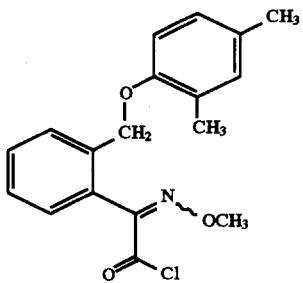

0.93 g (2.95 mmol) of α-methoximino-α-[2-(2,4-dimethylphenoxy-methyl)-phenyl]-acetic acid is mixed with 4.0 g (2.9 mmol) of thionyl chloride and 50 mg of dimethylformamide, and the mixture is stirred under reflux for 30 minutes. The more volatile components are then carefully removed by distillation under reduced pressure.

0.95 g of α-methoximino-α-[2-(2,4-dimethyl-phenoxymethyl)-phenyl]-acetoyl chloride is obtained as an oily residue.

102
Example (XV-2)

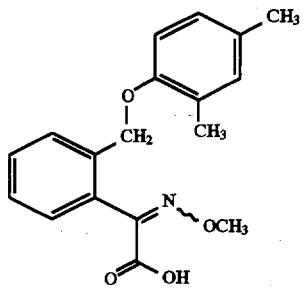

2.0 g (6.1 mmol) of methyl α-methoximino-α-[2-(2,4-dimethyl-phenoxy-methyl)-phenyl]-acetic acid are dissolved in 20 ml of isopropanol, and 30 ml of 1N sodium hydroxide solution are added. The mixture is stirred for 14 hours at 40° C. and then poured into water. The pH is then brought to 6 using 2N hydrochloric acid, and the product which has been obtained as crystals is isolated by filtration with suction.

1.5 g (78% of theory) of α-methoximino-α-[2-(2,4-dimethyl-phenoxy-methyl)-phenyl]-acetic acid are obtained.

$^1$H NMR (CDCl$_3$, δ): 3.9; 4.85 ppm.

Use Examples

Example A

*Pyrenophora teres* Test (barley)/protective

Solvent: 10 parts by weight of N-methyl-pyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are inoculated with a conidia spore suspension of *Pyrenophora teres*. The plants remain in an incubation cabin at 20° C. and 100% relative atmospheric humidity for 48 hours.

The plants are placed in a greenhouse at a temperature of approximately 20° C. and a relative atmospheric humidity of approximately 80%.

The test is evaluated 7 days after inoculation.

In this test, a degree of effectiveness of 100% was shown, for example, by the compound of Preparation Example 1 at an application rate of 400 g/ha.

Example B

Phytophthora Test (tomato)/systemic

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for systemic properties, the preparation of active compound is poured onto standard soil containing young plants which are ready for the experiment. 3 days after the treatment, the plants are inoculated with an aqueous spore suspension of *Phytophthora infestans.*

The plants remain in an incubation cabin at approximately 20° C. and 100% relative atmospheric humidity.

The test is evaluated 3 days after inoculation.

In this test, a degree of effectiveness of 58% was shown, for example, by the compound of Preparation Example 1 at an active compound concentration of 100 ppm.

Example C.

Pyricularia Test (rice)/systemic

Solvent: 12.5 parts by weight of acetone

Emulsifier: 0.3 part by weight of alkylaryl polyglycol ether

To produce a suitable preparation of active compound, 1 part by weight of active compound is mixed with the stated amounts of solvent, and the concentrate is diluted with water and the stated amount of emulsifier to the desired concentration.

To test for systemic properties, 40 ml of the preparation of active compound are poured onto standard soil in which young rice plants had been grown. 7 days after the treatment, the plants are inoculated with an aqueous spore suspension of *Pyricularia oryzae.* The plants then remain in a greenhouse at a temperature of 25° C. and a relative atmospheric humidity of 100% until they are evaluated.

The disease incidence is evaluated 4 days after inoculation.

In this test, a degree of effectiveness of 80% was shown, for example, by the compound of Preparation Example 1 at an application rate of 100 mg/100 ml.

We claim:

1. Azadioxacycloalkenes of the general formula (I)

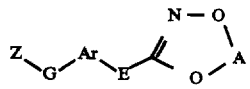

(I)

in which
- A represents optionally substituted dimethylene(ethane-2-diyl),
- Ar represents in each case optionally substituted arylene or heteroarylene,
- E represents a 1-alkene-1,1-diyl group with a radical $R^1$ in the 2-position, or a 2-aza-alkene-1,1-diyl group with a radical $R^2$ in the 2-position, or a 3-oxa- or 3-thia-1-propene-2,3-diyl group with a radical $R^1$ in the 1-position, or represents a 3-aza-1-propene-2,3-diyl group with a radical R in the 3-position and a radical $R^1$ in the 1-position, or represents a 1-aza-1-propene-2,3-diyl group with a radical $R^2$ in the 1-position, or represents a 3-oxa- or 3-thia-1-aza-propene-2,3-diyl group with a radical $R^2$ in the 1-position, or represents a 1,3-diaza-1-propene-2,3-diyl group with a radical R in the 3-position and a radical $R^2$ in the 1-position, or represents an optionally substituted imino group ("azamethylene", N—$R^3$), where
- R represents alkyl,
- $R^1$ represents hydrogen, halogen, cyano or in each case optionally substituted alkyl, alkoxy, alkylthio, alkylamino or dialkylamino,
- $R^2$ represents hydrogen, amino, cyano or in each case optionally substituted alkyl, alkoxy, alkylamino or dialkylamino, and
- $R^3$ represents hydrogen, cyano or in each case optionally substituted alkyl, alkenyl, alkinyl, cycloalkyl or cycloalkylalkyl,
- G represents a single bond, oxygen, or represents alkanediyl, alkenediyl, oxaalkenediyl, alkinediyl, each of which is optionally substituted by halogen, hydroxyl, alkyl, halogenoalkyl or cycloalkyl, or represents one of the groups below

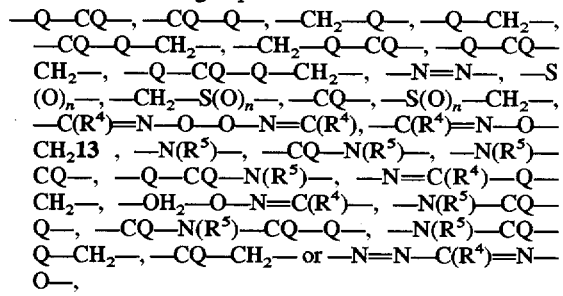

where
- n represents the numbers 0, 1 or 2,
- Q represents oxygen or sulphur,
- $R^4$ represents hydrogen, cyano, or represents alkyl, alkoxy, alkylthio, alkylamino, dialkylamino or cycloalkyl, each of which is optionally substituted, and
- $R^5$ represents hydrogen, hydroxyl, cyano, or represents alkyl, alkoxy or cycloalkyl, each of which is optionally substituted, and
- Z represents in each case optionally substituted alkyl, alkenyl, alkinyl, cycloalkyl, aryl or heterocyclyl.

2. Compounds of the formula (I) according to claim 1, in which

A represents domethylene(ethane-1,2-diyl) which is optionally substituted by halogen or by alkyl or halogenoalkyl, each of which has 1 to 4 carbon atoms, Ar represents in each case optionally substituted phenylene or naphthylene, or represents heteroarylene having 5 or 6 ring members of which at least one represents oxygen, sulphur or nitrogen and, if appropriate, one or two further ring members representing nitrogen, the substituents which are possible preferably being selected from the list below:

halogen, cyano, nitro, amino, hydroxyl, formyl, carboxyl, carbamoyl, thiocarbamoyl, in each case straight-chain or branched alkyl, alkoxy, alkylthio, alkylsulphinyl or alkylsulphonyl, each of which has 1 to 6 carbon atoms, in each case straight-chain or branched alkenyl, alkenyloxy or alkinyloxy, each of which has 2 to 6 carbon atoms, in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl, each of which has 1 to 6 carbon atoms in the individual alkyl moieties, or represents in each case divalent alkylene or dioxyalkylene, each of which has 1 to 6 carbon atoms and each of which is optionally monosubstituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms, E represents one of the groups below

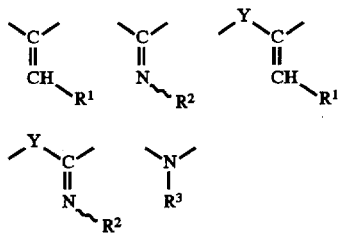

in which

Y represents oxygen, sulphur, methylene ($CH_2$) or alkylimino (N—R),

R represents alkyl having 1 to 6 carbon atoms, $R^1$ represents hydrogen, halogen, cyano, or represents alkyl, alkoxy, alkylthio, alkylamino or dialkylamino, each of which has 1 to 6 carbon atoms in the alkyl radicals and each of which is optionally substituted by halogen, cyano or $C_1$-$C_4$-alkoxy, $R^2$ represents hydrogen, amino, cyano, or represents alkyl, alkoxy, alkylamino or dialkylamino, each of which has 1 to 6 carbon atoms in the alkyl radicals and each of which is optionally substituted by halogen, cyano or $C_1$-$C_4$-alkoxy, and $R^3$ represents hydrogen, cyano, or represents alkyl, alkenyl or alkinyl, each of which has up to 6 carbon atoms and each of which is optionally substituted by halogen, cyano or $C_1$-$C_4$-alkoxy, or represents cycloalkyl or cycloalkylalkyl having 3 to 6 carbon atoms in the cycloalkyl moieties and, if appropriate, 1 to 4 carbon atoms in the alkyl moiety, each of these cycloalkyl or cycloalkylalkyl radicals optionally being substituted by halogen, cyano, carboxyl, $C_1$-$C_4$-alkyl or $C_1$-$C_4$-alkoxy-carbonyl, G represents a single bond, oxygen, or represents alkanediyl, alkenediyl, oxaalkenediyl, alkinediyl, each of which has up to 4 carbon atoms and each of which is optionally substituted by halogen, hydroxyl, $C_1$-$C_4$-alkyl, $C_1$-$C_4$-halogenoalkyl or $C_3$-$C_6$-cycloalkyl, or represents one of the groups below —Q—CQ—, —CQ—Q—, —$CH_2$—Q—, —Q—$CH_2$—, —CQ—Q—$CH_2$—, —$CH_2$—Q—CQ—, —Q—CQ—$CH_2$—, —Q—CQ—Q—$CH_2$—, —N=N—, —S(O)$_n$—, —$CH_2$—S(O)$_n$—, —CQ—, —S(O)$_n$—$CH_2$—, —C($R^4$)=N—O—O—N=C($R^4$), —C($R^4$)=N—O—$CH_2$—, —N($R^5$)—, —CQ—N($R^5$)—, —N($R^5$)—CQ—, —Q—CQ—N($R^5$)—, —N=C($R^4$)—Q—$CH_2$—, —$CH_2$—O—N=C($R^4$)—, —N($R^5$)—CQ—Q—, —CQ—N($R^5$)—CQ—Q—, —N($R^5$)—CQ—Q—$CH_2$—, —CQ—$CH_2$— or —N=N—C($R^4$)=N—O—, where n represents the numbers 0, 1 or 2, Q represents oxygen or sulphur, $R^4$ represents hydrogen, cyano, or represents alkyl, alkoxy, alkylthio, alkylamino or dialkylamino, each of which has 1 to 6 carbon atoms in the alkyl groups and each of which is optionally substituted by halogen, cyano or $C_1$-$C_4$-alkoxy, or represents cycloalkyl having 3 to 6 carbon atoms which is optionally substituted by halogen, cyano, carboxyl, $C_1$-$C_4$-alkyl or $C_1$-$C_4$-alkoxy-carbonyl, and $R^5$ represents hydrogen, hydroxyl, cyano, or represents alkyl having 1 to 6 carbon atoms which is optionally substituted by halogen, cyano or $C_1$-$C_4$-alkoxy, or represents cycloalkyl having 3 to 6 carbon atoms which is optionally substituted by halogen, cyano, carboxyl, $C_1$-$C_4$-alkyl or $C_1$-$C_4$-alkoxy-carbonyl, and Z represents alkyl having 1 to 8 carbon atoms which is optionally substituted by halogen, cyano, hydroxyl, amino, $C_1$-$C_4$-alkoxy, $C_1$-$C_4$-alkylthio, $C_1$-$C_4$-alkylsulphinyl or $C_1$-$C_4$-alkylsulphonyl (each of which is optionally substituted by halogen), or represents alkenyl or alkinyl, each of which has up to 8 carbon atoms and each of which is optionally substituted by halogen, or represents cycloalkyl having 3 to 6 carbon atoms which is optionally substituted by halogen, cyano, carboxyl, phenyl (which is optionally substituted by halogen, cyano, $C_1$-$C_4$-alkyl, $C_1$-$C_4$-halogenoalkyl, $C_1$-$C_4$-alkoxy or $C_1$-$C_4$-halogenoalkoxy), $C_1$-$C_4$-alkyl or $C_1$-$C_4$-alkoxy-carbonyl, or represents in each case optionally substituted phenyl, naphthyl or (optionally benzo-fused) heterocyclyl having 5 or 6 ring members of which at least one represents oxygen, sulphur or nitrogen and, if appropriate, one or two further ring members represent nitrogen, other possible substituents preferably being selected from the list below:

oxygen (as a replacement for two geminal-hydrogen atoms), halogen, cyano, nitro, amino, hydroxyl, formyl, carboxyl, carbamoyl, thiocarbamoyl, in each case straight-chain or branched alkyl, alkoxy, alkylthio, alkylsulphinyl or alkylsulphonyl, each of which has 1 to 6 carbon atoms, in each case straight-chain or branched alkenyl or alkenyloxy, each of which has 2 to 6 carbon atoms, in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched alkylamino, dialkylamino, alkylcarbonyl, alkyl carbonyloxy, alkoxy-carbonyl, alkylsulphonyloxy, hydroximinoalkyl or alkoximinoalkyl, each of which has 1 to 6 carbon atoms in the individual alkyl moieties, in each case divalent alkylene or dioxyalkylene, each of which has 1 to 6 carbon atoms and each of which is optionally monosubstituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms, or cycloalkyl having 3 to 6 carbon atoms, heterocyclyl or heterocyclylmethyl, each of which has 3 to 7 ring members, of which in each case 1 to 3 are identical or different hereto atoms—in particular nitrogen, oxygen and/or sulphur-, and phenyl, phenoxy, benzyl, benzyloxy, phenylethyl or phenylethyloxy, each of which is optionally monosubstituted or polysubstituted in the phenyl moiety by identical or different substituents from the series consisting of halogen, cyano, nitro, carboxyl, carbamoyl and/or straight-chain or branched alkyl having 1 to 4 carbon atoms and/or straight-chain

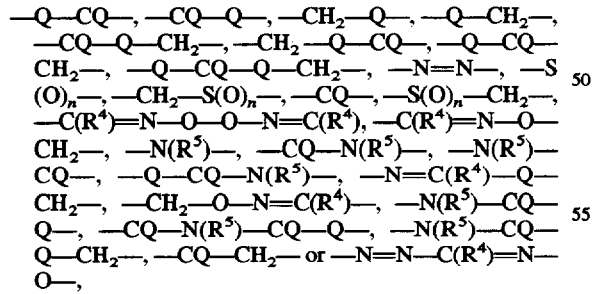

or branched halogenoalkyl having 1 to 4 carbon atoms and 1 to 9 identical or different halogen atoms and/or straight-chain or branched alkoxy having 1 to 4 carbon atoms and/or straight-chain or branched halogenoalkoxy having 1 to 4 carbon atoms and 1 to 9 identical or different halogen atoms and/or alkylcarbonyl or alkoxycarbonyl, each of which has up to 5 carbon atoms.

3. Compounds of the formula (i) according to claim 1, in which

A represents dimethylene (ethane-1,2-diyl) which is optionally substituted by fluorine, chlorine, methyl, ethyl or trifluoromethyl, Ar represents in each case optionally substituted ortho-, meta- or para-phenylene, or represents furandiyl, thiophenediyl, pyrrolediyl, pyrazolediyl, triazolediyl, oxazolediyl, isoxazolediyl, thiazolediyl, isothiazolediyl, oxadiazolediyl, thiadiazolediyl, pyridinediyl, pyrimidinediyl, pyridazinediyl, pyrazinediyl, 1,3,4-triazinediyl or 1,2,3-triazinediyl, the possible substituents being selected, in particular, from the list below:

fluorine, chlorine, cyano, methyl, ethyl, trifluoromethyl, methoxy, ethoxy, methylthio, methylsulphinyl or methylsulphonyl, E represents one of the groups below

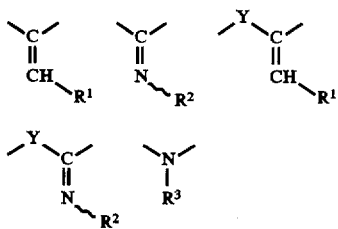

in which

Y represents oxygen, sulphur, methylene ($CH_2$) or alkylimino (N—R),

R represents methyl, ethyl, n- or i-propyl, or n-, i- or s-butyl, $R^1$ represents hydrogen, fluorine, chlorine, bromine, cyano, or represents methyl, ethyl, propyl, methoxy, ethoxy, methylthio, ethylthio, methylamino, ethylamino or dimethylamino, each of which is optionally substituted by fluorine, chlorine, cyano, methoxy or ethoxy, $R^2$ represents hydrogen, amino, cyano, or represents methyl, ethyl, methoxy, ethoxy, methyleunino, ethylamino or dimethylamino, each of which is optionally substituted by fluorine, chlorine, cyano, methoxy or ethoxy, and $R^3$ represents hydrogen, cyano, or represents methyl, ethyl, n- or i-propyl, or n-, i- or s-butyl, each of which is optionally substituted by fluorine, cyano, methoxy or ethoxy, represents allyl or propargyl, or represents cyclopropyl, cyclobutyl, cyclopentyl, cyclohexyl, cyclopropylmethyl, cyclobutylmethyl, cyclopentylmethyl or cyclohexylmethyl, each of which is optionally substituted by fluorine, chlorine, cyano, carboxyl, methyl, ethyl, n- or i-propyl, methoxycarbonyl or ethoxy-carbonyl, G represents a single bond, oxygen, or represents methylene, dimethylene (ethane-1,2-diyl), ethene-1,2-diyl, ethine-1,2-diyl, each of which is optionally substituted by fluorine, chlorine, hydroxyl, methyl, ethyl, n- or i-propyl, trifluoromethyl, cyclopropyl, cyclobutyl, cyclopentyl or cyclohexyl, or represents one of the groups below —Q—CQ—, —CQ—Q—, —$CH_2$—, —Q—$CH_2$—, —CQ—Q—$CH_2$—, —$CH_2$—Q—CQ—, —Q—CQ—$CH_2$—, —Q—CQ—Q—$CH_2$—, —N=N—, —S(O)$_n$—, —$CH_2$—S(O)$_n$—, —CQ—, —S(O)$_n$—$CH_2$—, —C($R^4$)=N—O—C—N=C($R^4$), —C($R^4$)=N—O—$CH_2$—, —N($R^5$)—, —CQ—N($R^5$)—, —N($R^5$)—CQ—, —Q—CQ—N($R^5$)—, —N=C($R^4$)—Q—$CH_2$—, —$CH_2$—O—N=C($R^4$)—, —N($R^5$)—CQ—Q—, —CQ—N($R^5$)—CQ—Q—, —N($R^5$)—CQ—Q—$CH_2$—, —CQ—$CH_2$ or —N=N—C($R^4$)=N—O—, where n represents the numbers 0, 1 or 2, Q represents oxygen or sulphur, $R^4$ represents hydrogen, cyano, or represents methyl, ethyl, n- or i-propyl, n-, i- or s-butyl, methoxy, ethoxy, propoxy, butoxy, methylthio, ethylthio, propylthio, butylthio, methylamino, ethylamino, propylamino,-di-methylamino or diethylamino, each of which is optionally substituted by fluorine, chlorine, cyano, methoxy or ethoxy, or represents cyclopropyl, cyclobutyl, cyclopentyl or cyclohexyl, each of which is optionally substituted by fluorine, chlorine, cyano, carboxyl, methyl, ethyl, n- or i-propyl, methoxycarbonyl or ethoxy- carbonyl, and $R^5$ represents hydrogen, hydroxyl, cyano, or represents methyl, ethyl, n- or i-propyl or n-, i-, s - or t-butyl, each of which is optionally substituted by fluorine, chlorine, cyano, methoxy or ethoxy, or represents cyclopropyl, cyclobutyl, cyclopentyl or cyclohexyl, each of which is optionally substituted by fluorine, chlorine, cyano, carboxyl, methyl, ethyl, n- or i-propyl, methoxycarbonyl or ethoxycarbonyl, and Z represents methyl, ethyl n- or i-propyl or n-, i-, s- or t-butyl, each of which is optionally substituted by fluorine, chlorine, bromine, cyano, hydroxyl, amino, methoxy, ethoxy, methylthio, ethylthio, methylsulphinyl, ethylsulphinyl, methylsulphonyl or ethylsulphonyl (each of which is optionally substituted by fluorine and/or chlorine), or represents allyl, crotonyl, 1-methyl-allyl, propargyl or 1-methyl-propargyl, each of which is optionally substituted by fluorine, chlorine or bromine, or represents cyclopropyl, cyclobutyl, cyclopentyl or cyclohexyl, each of which is optionally substituted by fluorine, chlorine, bromine, cyano, carboxyl, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, n- or i-propyl, methoxy-carbonyl or ethoxy-carbonyl, or represents in each case optionally substituted phenyl, naphthyl, furyl, tetrahydrofuryl, benzofuryl, tetrahydropyranyl, thienyl, benzothienyl, pyrrolyl, dihydropyrrolyl, tetrahydropyrrolyl, benzopyrrolyl, benzodihydropyrrolyl, oxazolyl, benzoxazolyl, isoxazolyl, thiazolyl, benzothiazolyl, isothiazolyl, imidazolyl, benzimidazolyl, oxadiazolyl, thiadiazolyl, pyridinyl, pyrimidinyl, pyridazinyl, pyrazinyl, 1,2,3-triazinyl, 1,2,4-triazinyl or 1,3,5-triazinyl, the possible substituents in each case preferably being selected from the list below:

oxygen (as a replacement for two geminal hydrogen atoms), fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluoromethylthio, trifluoro-methylthio, trifluoromethylsulphinyl or trifluoro-methylsulphonyl, methylamino, ethylamino, n- or i-propylamino, dimethylamino, diethylamino, acetyl, propionyl, acetyloxy, methoxycarbonyl, ethoxy-carbonyl, methylsulphonyloxy, ethylsulphonyl-oxy, hydroximinomethyl, hydroximinoethyl, methoximino-methyl, ethoximinomethyl, methoximinoethyl or ethoximinoethyl; or trimethylene (propane-1,3-diyl), methylenedioxy or ethylenedioxy, each of which is optionally monosubstituted or polysubstituted by identical or different substituents from the series consisting of fluorine, chlorine, methyl, ethyl or n- or i-propyl, or cyclopropyl, cyclobutyl, cyclopentyl or cyclohexyl, and phenyl, phenoxy, benzyl or benzyloxy, each of which is optionally monosubstituted or polysubstituted in the phenyl moiety by identical or different substituents from the series consisting of fluorine, chlorine, bromine, cyano, nitro, carboxyl, carbamoyl, methyl, ethyl, n- or i-propyl, n-, i-, s- or t-butyl, trifluoromethyl, methoxy, ethoxy, n- or i-propoxy, difluoromethoxy, trifluoromethoxy, acetyl, methoxycarbonyl or ethoxycarbonyl.

4. Compounds of the formula (I) according to claim 1, in which

A represents dimethylene (ethane-1,2-diyl),

Ar represents ortho-phenylene, pyridine-2,3-diyl or thiophene-2,3-diyl,

E represents one of the groups below

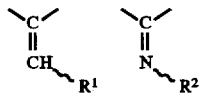

in which

R¹ and R² in each case represent methoxy,

G represents oxygen, methylene or one of the groups below

—CH₂—O—, —O—CH₂—, —S(O)ₙ—, —CH₂—S(O)ₙ—, —S(O)ₙ—CH₂—, —C(R⁴)=N—O—, —O—N=C(R⁴)—, —C(R⁴)=N—O—CH₂—, —N(R⁵)— or —CH₂—O—N=C(R⁴)—, where n represents the numbers 0, 1 or 2, R⁴ represents hydrogen, methyl or ethyl and R⁵ represents hydrogen, methyl or ethyl, and Z represents in each case optionally substituted phenyl, pyridinyl, pyrimidinyl, pyridazinyl, pyrazinyl, 1,2,3-triazinyl, 1,2,4-triazinyl or 1,3,5-triazinyl, the possible substituents preferably being selected from the list below:

fluorine, chlorine, bromine, cyano, methyl, ethyl, n- or i-propyl, n-, i-, s- or t-butyl; methoxy, ethoxy, n- or i-propoxy, methylthio, ethylthio, n- or i- propylthio, methylsulphinyl, ethylsulphinyl, methylsulphonyl or ethylsulphonyl, trifluoromethyl, difluoromethoxy, trifluoromethoxy, difluoromethylthio, trifluoromethylthio, trifluoromethylsulphinyl or trifluoromethylsulphonyl, methoxycarbonyl, ethoxycarbonyl, methoximinomethyl, ethoximinomethyl, methoximinoethyl or ethoximinoethyl, or methylenedioxy or ethylenedioxy, each of which is optionally monosubstituted or polysubstituted by identical or different substituents from the series consisting of fluorine, chlorine, methyl or ethyl, and phenyl, phenoxy, benzyl or benzyloxy, each of which is optionally monosubstituted or polysubstituted in the phenyl moiety by identical or different substituents from the series consisting of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy.

5. Process for the preparation of azadioxacycloalkenes of the general formula (I) according to claim 1, characterized in that (a) carboxylic acid derivatives of the general formula (II)

in which

Ar, E, G and Z have the abovementioned meaning and

R represents alkyl are reacted, in a first step, with hydroxylamine or with a hydrohalide thereof, if appropriate in the presence of an acid acceptor and if appropriate in the presence of a diluent, and the product of the first step is reacted in situ, i.e. without intermediate isolation, in a second step with disubstituted alkanes of the general formula (III)

in which

A has the abovementioned meaning and

X represents halogen, alkylsulphonyloxy or arylsulphonyloxy, if appropriate in the presence of an acid acceptor and, if appropriate, in the presence of a diluent, or in that, (b) in the event that, in formula (I), G represents oxygen or the group —CH₂—O— and A, Ar, E and Z have the meaning given in claim 1, hydroxyaryl compounds of the general formula (IV)

in which

A, Ar and E have the abovementioned meaning, are reacted with compounds of the general formula (V)

in which

X and Z have the abovementioned meaning and m represents the numbers 0 or 1, if appropriate in the presence of an acid acceptor and, if appropriate, in the presence of a diluent, and, if appropriate, substitution reactions are subsequently carried out on the group Z by customary methods, or in that, (c) in the event that, in formula (I), G represents the group —Q—CH$_2$— and A, Ar, E and Z have the abovementioned meaning, halogenomethyl compounds of the general formula (VI)

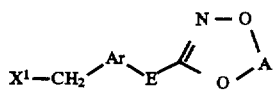  (VI)

in which

A, Ar and E have the abovementioned meaning and
X$^1$ represents halogen, are reacted with compounds of the general formula (VII)

  (VII)

in which

Q and Z have the abovementioned meaning, if appropriate in the presence of an acid acceptor and, if appropriate, in the presence of a diluent, or in that (d) hydroxyalkoxyamides of the general formula (VIII)

  (VIII)

in which

A, Ar, E, G and Z have the abovementioned meaning, are subjected to a dehydrating cyclization reaction with a dehydrating agent, if appropriate in the presence of a diluent.

6. A fungicidal composition comprising a fungicidally effective amount of a compound according to claim 1 and a diluent.

7. A method of combatting fungi which comprises applying to such fungi or to a fungus habitat a fungicidally effective amount of a compound according to claim 1 and a diluent.

* * * * *

UNITED STATES PATENT AND TRADEMARK OFFICE
CERTIFICATE OF CORRECTION

PATENT NO. : 5,679,676
DATED : October 21, 1997
INVENTOR(S) : Kruger, et al.

It is certified that error appears in the above-indentified patent and that said Letters Patent is hereby corrected as shown below:

| | |
|---|---|
| Col. 103, line 41 | After " ethane- " insert -- 1, -- |
| Col. 103, line 47 | After " 2-aza- " insert -- 1- -- |
| Col. 104, line 14 | Delete " $CH_2 13$ " and substitute -- $CH_2-$ -- |
| Col. 104, line 16 | Delete " $OH_2-O-N=C(R^4)-$ " and substitute -- $CH_2-O-N=C(R4)-$ -- |
| Col. 104, line 34 | Delete " domethylene(ethane-1,2-diyl) " substitute -- dimethylene(ethane-1,2-diyl) -- |
| Col. 106, line 60 | Delete " hereto " and substitute -- hetero -- |
| Col. 107, line 9 | Delete " (i) " and substitute -- (I) -- |
| Col. 108, line 5 | After " $CH_2-$ " insert -- Q- -- |

UNITED STATES PATENT AND TRADEMARK OFFICE
CERTIFICATE OF CORRECTION

PATENT NO. : 5,679,676
DATED : October 21, 1997
INVENTOR(S) : Kruger, et al.

It is certified that error appears in the above-indentified patent and that said Letters Patent is hereby corrected as shown below:

Col. 108, line 9  Delete " $-C(R^4)=N-O-C-N=C(R^4)$ " and substitute -- $-C(R^4)=N-O-O-N=C(R^4)$ --

Col. 108, line 11  Delete " $(R^4)$ " and substitute -- $(R^4)$ --

Signed and Sealed this

Thirtieth Day of March, 1999

Q. TODD DICKINSON

Attest:

*Attesting Officer*　　　*Acting Commissioner of Patents and Trademarks*